(12) United States Patent
Lahann et al.

(10) Patent No.: US 8,187,708 B2
(45) Date of Patent: *May 29, 2012

(54) MICROPHASIC MICRO-COMPONENTS AND METHODS FOR CONTROLLING MORPHOLOGY VIA ELECTRIFIED JETTING

(75) Inventors: Joerg Lahann, Ann Arbor, MI (US); Abbass Kazemi, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/506,712

(22) Filed: Jul. 21, 2009

(65) Prior Publication Data

US 2010/0015447 A1 Jan. 21, 2010

Related U.S. Application Data

(63) Continuation-in-part of application No. 11/763,842, filed on Jun. 15, 2007, which is a continuation-in-part of application No. 11/272,194, filed on Nov. 10, 2005, now Pat. No. 7,767,017.

(60) Provisional application No. 60/626,792, filed on Nov. 10, 2004, provisional application No. 60/651,288, filed on Feb. 9, 2005, provisional application No. 60/814,706, filed on Jun. 16, 2006.

(51) Int. Cl.
*B29C 59/10* (2006.01)
*B32B 1/00* (2006.01)

(52) U.S. Cl. ........ 428/403; 424/489; 424/400; 424/490; 424/501

(58) Field of Classification Search ................ None
See application file for complete search history.

(56) References Cited

U.S. PATENT DOCUMENTS 3,060,429 A 10/1962 Winston
(Continued)

FOREIGN PATENT DOCUMENTS

EP 1809719 7/2007
(Continued)

OTHER PUBLICATIONS

Kyung-Ho Roh et al. (Nature Materials, 4, 759-763 (2005), Published online: Sep. 25, 2005).*

(Continued)

*Primary Examiner* — Melvin Mayes
*Assistant Examiner* — Yun Qian
(74) *Attorney, Agent, or Firm* — Harness, Dickey & Pierce, P.L.C.

(57) ABSTRACT

The disclosure provides methods for preparation of multiphasic micro-components, such as core-shell or anisotropic (e.g., Janus) multiphasic particles with well-defined structures using electrohydrodynamic co-jetting of two polymer solutions containing polyelectrolytes. Suitable polyelectrolytes include polyacrylic acid (PAA), poly(acrylamide acrylic acid (PAAm), and/or poly(acryl amide-co-acrylic acid) (PAAm-AA), sodium polystyrene sulfonate (PSS), polyethylene imine (PEI), polypeptides, copolymers and combinations of these. Control of certain variables, such as relative conductivities of the two jetting solutions, controls the particle morphologies formed, leading to a predetermined phase orientation for the same polymer system. In certain aspects, after cross-linking, core-shell particles are stable in aqueous solutions and exhibit reproducible swelling behavior, while maintaining the original core-shell geometry. In addition, micro-components formed in accordance with the present teachings are pH-responsive based on external environmental pH. Thus, such micro-components are useful for a variety of different applications, including micro- and nano-active ingredient delivery systems.

21 Claims, 7 Drawing Sheets

U.S. PATENT DOCUMENTS

| | | | |
|---|---|---|---|
| 4,621,268 | A | 11/1986 | Keeling et al. |
| 5,560,543 | A | 10/1996 | Smith et al. |
| 5,741,138 | A | 4/1998 | Rice et al. |
| 5,813,614 | A | 9/1998 | Coffee |
| 6,007,845 | A * | 12/1999 | Domb et al. ................ 424/501 |
| 6,063,365 | A | 5/2000 | Shefer et al. |
| 6,107,102 | A | 8/2000 | Ferrari |
| 6,132,702 | A | 10/2000 | Witt et al. |
| 6,252,129 | B1 | 6/2001 | Coffee |
| 6,267,724 | B1 | 7/2001 | Taylor |
| 6,306,993 | B1 | 10/2001 | Rothbard et al. |
| 6,391,471 | B1 | 5/2002 | Hiroaka et al. |
| 6,491,902 | B2 | 12/2002 | Shefer et al. |
| 6,548,264 | B1 * | 4/2003 | Tan et al. .................... 435/7.21 |
| 6,589,562 | B1 | 7/2003 | Shefer et al. |
| 6,669,961 | B2 * | 12/2003 | Kim et al. .................... 424/489 |
| 6,685,921 | B2 | 2/2004 | Lawlor |
| 6,703,235 | B2 | 3/2004 | Luebke et al. |
| 6,766,817 | B2 | 7/2004 | da Silva et al. |
| 6,811,090 | B2 | 11/2004 | Yogi et al. |
| 6,825,161 | B2 | 11/2004 | Shefer et al. |
| 6,918,404 | B2 | 7/2005 | Dias da Silva et al. |
| 7,066,586 | B2 | 6/2006 | da Silva et al. |
| 7,413,868 | B2 | 8/2008 | Kauvar et al. |
| 7,767,017 | B2 | 8/2010 | Lahann et al. |
| 2006/0201390 | A1 | 9/2006 | Lahann et al. |
| 2007/0054119 | A1 | 3/2007 | Garstecki et al. |
| 2007/0112180 | A1 | 5/2007 | Gray et al. |
| 2007/0167340 | A1 | 7/2007 | Barthel et al. |
| 2007/0231355 | A1 | 10/2007 | Quadir et al. |
| 2007/0237800 | A1 | 10/2007 | Lahann |
| 2008/0242774 | A1 | 10/2008 | Lahann et al. |
| 2010/0038830 | A1 | 2/2010 | Lahann et al. |

FOREIGN PATENT DOCUMENTS

| | | |
|---|---|---|
| JP | 2004-505761 | 2/2004 |
| JP | 2005504090 | 2/2005 |
| JP | 2008520407 | 6/2008 |
| WO | WO 02/13786 | 2/2002 |
| WO | WO 03/026611 | 4/2003 |
| WO | WO 2006/003403 | 1/2006 |
| WO | WO 2006/137936 | 12/2006 |
| WO | WO 2007/149310 | 12/2007 |
| WO | WO 2009/055693 | 4/2009 |
| WO | WO 2009/151421 | 12/2009 |
| WO | WO 2010/011641 | 1/2010 |

OTHER PUBLICATIONS

Applicants' Response to Office Action issued in cross-referenced matter U.S. Appl. No. 11/763,842 (U.S. Pub. No. 2007/0237800) on Jun. 18, 2010 as filed on Nov. 18, 2010.

Applicants' Response to Office Action issued in cross-referenced matter U.S. Appl. No. 12/137,121 (U.S. Pub. No. 2008/0242774) on May 25, 2010 as filed on Nov. 18, 2011.

Applicants' Response to Office Action issued in cross-referenced matter U.S. Appl. No. 12/257,945 (U.S. Pub. No. 2010/0038830) on May 14, 2010 as filed on Nov. 12, 2010.

Moffat, Kristen L. et al., "Novel Nanofiber-Based Scaffold for Rotator Cuff Repair and Augmentation," Tissue Engineering: Part A, vol. 15, No. 1, pp. 115-126 (Jan. 2009). (Published Online Sep. 13, 2008).

Moffat, Kristen L. et al., "Orthopedic Interface Tissue Engineering for the Biological Fixation of Soft Tissue Grafts," Clin. Sports Med., vol. 28, No. 1, pp. 157-176 (Jan. 2009).

Notice of Allowance issued on Jan. 25, 2011 in cross-referenced matter U.S. Appl. No. 12/137,121 (U.S. Pub. No. 2008/0242774).

Office Action issued in cross-referenced matter U.S. Appl. No. 11/763,842 (U.S. Pub. No. 2007/0237800) on Jan. 20, 2011.

Office Action issued in cross-referenced matter U.S. Appl. No. 12/257,945 (U.S. Pub. No. 2010/0038830) on Mar. 17, 2011.

Office Action issued in cross-referenced matter U.S. Appl. No. 12/821,688 (U.S. Pub. No. 2011/0062608) on Mar. 3, 2011.

The International Search Report and Written Opinion of the International Searching Authority issued on Jan. 13, 2011 in related corresponding cross-referenced matter International Application No. PCT/US2010/032971 (Publication No. WO/2010/127119).

X., Mo et al., "PCL-PGLA composite tubular scaffold preparation and biocompatibility investigation," Int. J. Artif. Organs, vol. 29, No. 8 pp. 790-799 (Aug. 2006). Abstract Only.

Barrero, A. et al., "Micro- and Nanoparticles via Capillary Flows," Annu. Rev. Fluid Mech., vol. 39, pp. 89-106 (2007).

Berkland C., et al., "Controlling surface nano-structure using flow-limited field-injection electrostatic spraying (FFESS) of poly(D,L-lactide-co-glycolide)," Biomaterials, vol. 25, No. 25, pp. 5649-5658 (Nov. 2004).

Bhaskar, S. et al., "Spatioselective Modification of Bicompartmental Polymer Particles and Fibers via Huisgen 1,3-Dipolar Cycloaddition," Macromol. Rapid Commun., vol. 29, No. 20, pp. 1655-1660 (Oct. 22, 2008).

Binks, B. P. et al., "Particles Adsorbed at the Oil-Water Interface: A Theoretical Comparison between Spheres of Uniform Wettability and "Janus" Particles," Langmuir, vol. 17, pp. 4708-4710 (2001).

Casagrande, C. et al., "Janus Beads: Realization and Behaviour at Water/Oil Interfaces," Europhys. Lett., vol. 9, No. 3, pp. 251-255 (1989).

Cayre, O. et al, "Fabrication of Dipolar Colloid Particles by Microcontact Printing," Chem. Commun., pp. 2296-22997 (2003).

Cayre, O. et al., "Fabrication of Asymmetrically Coated Colloid Particles by Microcontact Printing Techniques," J. Mater. Chem., vol. 13, pp. 2445-2450 (2003).

Cloupeau, M. et al., "Electrohydrodynamic spraying functioning modes—a critical-review," J. Aerosol Sci., vol. 25, No. 6, pp. 1021-1036 (1994).

Cloupeau, M. et al., "Electrostatic spraying of liquids—Main functioning modes, " J. Electrostatics, vol. 25, pp. 165-184 (1990).

De La Mora, J. F. et al., "The current emitted by highly conducting Taylor cones," J. Fluid Mech., vol. 260, pp. 155-184 (1994).

Erhardt, R. et al., "Amphiphillic Janus Micelles With Polystyrene and Poly(methacrylic acid) Hemispheres," J. Am. Chem. Soc., vol. 125, pp. 3260-3267 (2003).

Erhardt, R. et al., "Janus Micelles," Macromolecules, vol. 34, pp. 1069-1075 (2001).

Farokhzad, O. et al., "Nanoparticle-Aptamer Bioconjugates: A New Approach for Targeting Prostate Cancer Cells," Cancer Research, vol. 64, pp. 7668-7672 (2004).

Fridrikh, S. V. et al., "Controlling the Fiber Diameter during Electrospinning," Phys. Rev. Lett., vol. 90, No. 14, pp. 144502-1 to 144502-4 (2003).

Gomez, A. et al., "Charge and fission of droplets in electrostatic sprays," Phys. Fluids, vol. 6, No. 1, pp. 404-414 (1994).

Gunatillake, P. et al., "Biodegradable Synthetic Polymers for Tissue Engineering," European Cells and Materials, vol. 5, pp. 1-16 (2003).

Guo, K. et al., "Aptamer-based capture molecules as a novel coating strategy to promote cell adhesion," J. Cell. Mol. Med., vol. 9, No. 3, pp. 731-736 (2005).

Gupta, P. et al, "Some investigations on the fiber formation by utilizing a side-by-side bicomponent electrospinning approach," Polymer, vol. 44, pp. 6353-6359 (2003).

Hicke, B. et al., "Tumor Targeting by an Aptamer," J. of Nuclear Med., vol. 47, No. 4, pp. 668-678 (2006).

Hohman, M. M. et al., "Electrospinning and electrically forced jets. II. Applications," Physics of Fluids, vol. 13, No. 8, pp. 2221-2236 (2001).

Hohman, M. M. et al., "Electrospinning and electrically forced jets. I. Stability Theory," Physics of Fluids, vol. 13, No. 8, pp. 2201-2220 (2001).

Huang, Z. et al., "A review on polymer nanofibers by electrospinning and their applications in nanocomposites," Comp. Sci. Tech., vol. 63, pp. 2223-2253 (2003).

International Search Report and Written Opinion of the International Searching Authoritiy issued on Mar. 8, 2010 in related and cross-referenced matter PCT/US2009/051238 (WO2010/011641).

International Search Report and Written Opinion of the International Searching Authoritiy issued on Mar. 11, 2009 cross-referenced matter PCT/US2008/007372 (WO2009/151421).

International Search Report and Written Opinion of the International Searching Authoritiy issued on Jul. 23, 2009 in cross-referenced matter PCT/US2008/081145 (WO2009/055693).

Kazemi, A., et al., "Environmentally Responsive Core/Shell Particles via Electrohydrodynamic Co-jetting of Fully Miscible Polymer Solutions," Small, vol. 4, No. 10, pp. 1756-1762 (2008).

Lahann, J. et al., "Biphasic nanoparticles made by electrified jetting," 2005 APS March meeting, (Mar. 22, 2005).

Larsen, G. et al., "A Method for Making Inorganic and Hybrid (Organic/Inorganic) Fibers and Vesicles with Diameters in the Submicrometer and Micrometer Range via Sol-Gel Chemistry and Electrically Forced Liquid Jets," J. Am. Chem. Soc., vol. 125, pp. 1154-1155 (2003).

Loscertales, I. et al., "Electrically Forced Coaxial Nanojets for One-Step Hollow Nanofiber Design," J. Am. Chem. Soc., vol. 126, pp. 5376-5377 (2004).

Loscertales, I. et al., "Micro/nano Encapsulation via Electrified Coaxial Liquid Jets," Science, vol. 295, pp. 1695-1698 (2002).

Loscertales, I. et al., "Production of complex nano-structures by electro-hydro-dynamics," Mater. Res. soc. Symp. Proc., vol. 860E. pp. LL5.9.1-LL5.9.6 (2005).

Marin, A. et al., "Simple and Double Emissions via Coaxial Jet Electrosprays," The Amer. Phys. Soc., vol. 98, pp. 014502-1 to 014502-4 (2007).

Nie, Z. et al., "Janus and Ternary Particles Generated by Microfluidic Synthesis: Design, Synthesis, and Self-Assembly," J. Am. Chem. Soc., vol. 128, pp. 9408-9412 (2006).

Nisisako, T. et al., "Synthesis of Monodisperse Bicolored Janus Particles with Electrical Anisotropy Using a Microfluidic Co-Flow System," Adv. Mater., vol. 18, pp. 1152-1156 (2006).

Non-Final Office Action for U.S. Appl. No. 12/137,121 (U.S. Pub. No. 2008/0242774) dated May 25, 2010.

Non-Final Office Action for U.S. Appl. No. 12/257,945 (U.S. Pub. No. 2010/0038830) dated May 14, 2010.

Non-Final Office Action for U.S. Appl. No. 12/137,121 (U.S. Pub. No. 2008/0242774) dated Feb. 3, 2010.

Non-Final Office Action issued in U.S. Appl. No. 11/763,842 (U.S. Pub. No. 2007/0237800) on Jun. 18, 2010.

Notice of Rejection issued on Jul. 27, 2010 in related matter Japanese Patent Publication JP 2007-540191. English translation provided by Kashiwabara International Patent Bureau.

Palm, L. et al., "An Optical Method for Measuring Drop Flight Stability in a Continuous Ink Jet," Journal for Imaging Science and Technology, vol. 41, No. 1 (Jan./Feb. 1997).

Paunov, V. et al., "Novel Technique for Preparation of Dipolar Microparticles by Polymerization of Polarised Emulsions," Abstract Central, 1 page (undated).

Perro, A. et al., "Design and Synthesis of Janus Micro- and Nanparticles," The Royal Soc. of Chem., vol. 15, pp. 3745-3760 (2005).

Response filed on Mar. 3, 2010 to Non-Final Office Action dated Feb. 3, 2010 for U.S. Appl. No. 12/137,121 (U.S. Pub. No. 2008/0242774).

Roh, K. et al., "Biphasic Janus Particles with Nanoscale Anisotrophy," Nature Materials, vol. 4, pp. 759-763 (2005).

Roh, K. et al., "Triphasic Nanocolloids," J. Am. Chem. Soc., vol. 128, pp. 6796-6797 (2006).

Rosell-Llompart, J. et al., "Generation of Monodisperse Droplets 0.3 to 4 μm in Diameter from Electrified Cone-Jets of Highly Conducting and Viscous Liquids," J. Aerosol Sci., vol. 25, No. 6, pp. 1093-1119 (1994).

Shepherd, R. F. et al., "Microfluidic Assembly of Homogeneous and Janus Colloid-Filled Hydrogel Granules," Langmuir, vol. 22, pp. 8618-8622 (2006).

Shin, Y. M. et al., "Electrospinning: A whipping fluid jet generates submicron polymer fibers," Appl. Phys. Lett, vol. 78, No. 8, pp. 1149-1151 (2001).

Sun, Q. et al., "Design of Janus Nanoparticles with Atomic Precision," 2008 APS March meeting (Mar. 13, 2008).

Sun, Z. C. et al., "Compound Core-Shell Polymer Nanofibers by Co-Electrospinning," Adv. Mater., vol. 15, No. 22, pp. 1929-1932 (2003).

Takei, H. et al., "Gradient Sensitive Microscopic Probes Prepared by Gold Evaporation and Chemisorption on Latex Spheres," Langmuir, vol. 13, No. 7, pp. 1865-1868 (1997).

Ulrich, K. et al., "Polymeric Systems for Controlled Drug Release," Chem. Rev., vol. 99, pp. 3181-3198 (1999).

Wako Pure Chemical Industries, Ltd., Biodegradable Polymers (PLA-PLGA) http://www.wako-chem.co.jp/specialty/plga/index.htm.

Zeleny, J., "Instability of electrified liquid surfaces," Phys. Rev., vol. 10, No. 1, pp. 1-6 (1917).

\* cited by examiner

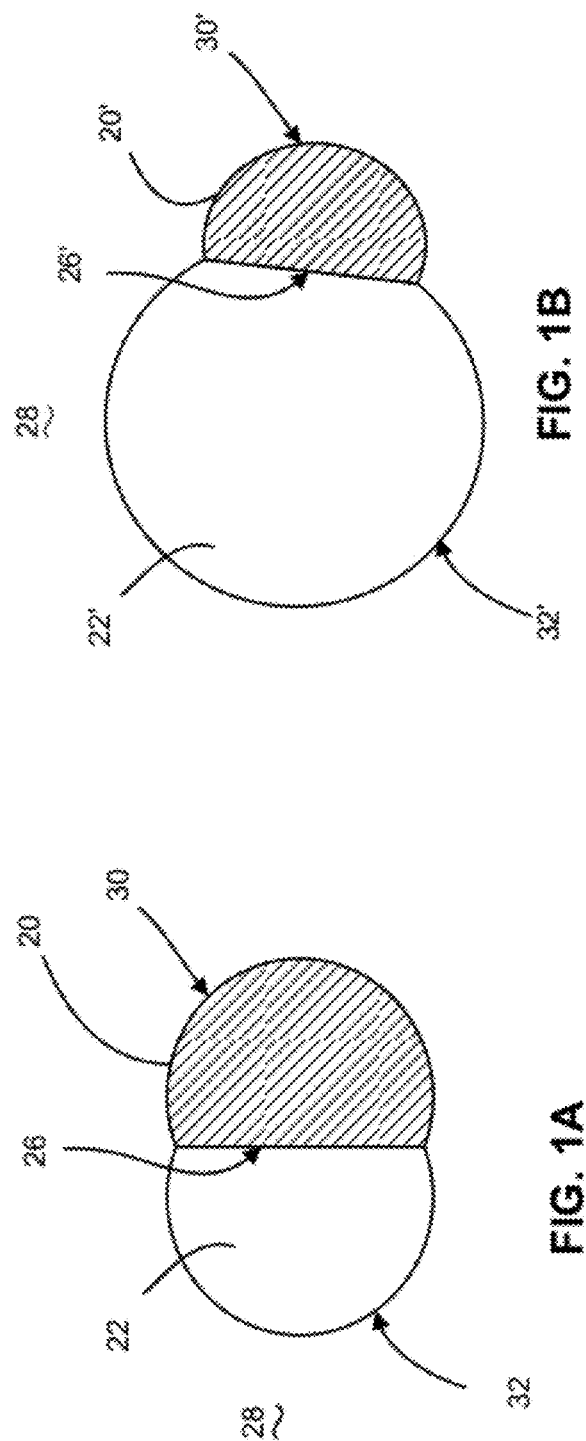
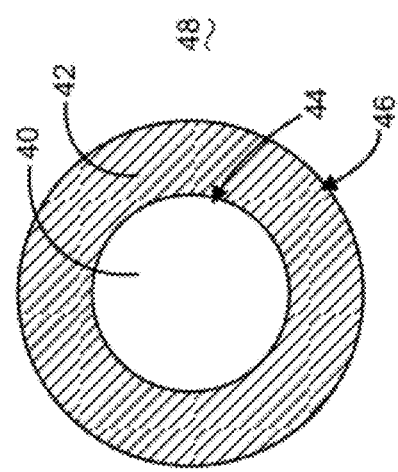
FIG. 1A
FIG. 1B
FIG. 1C

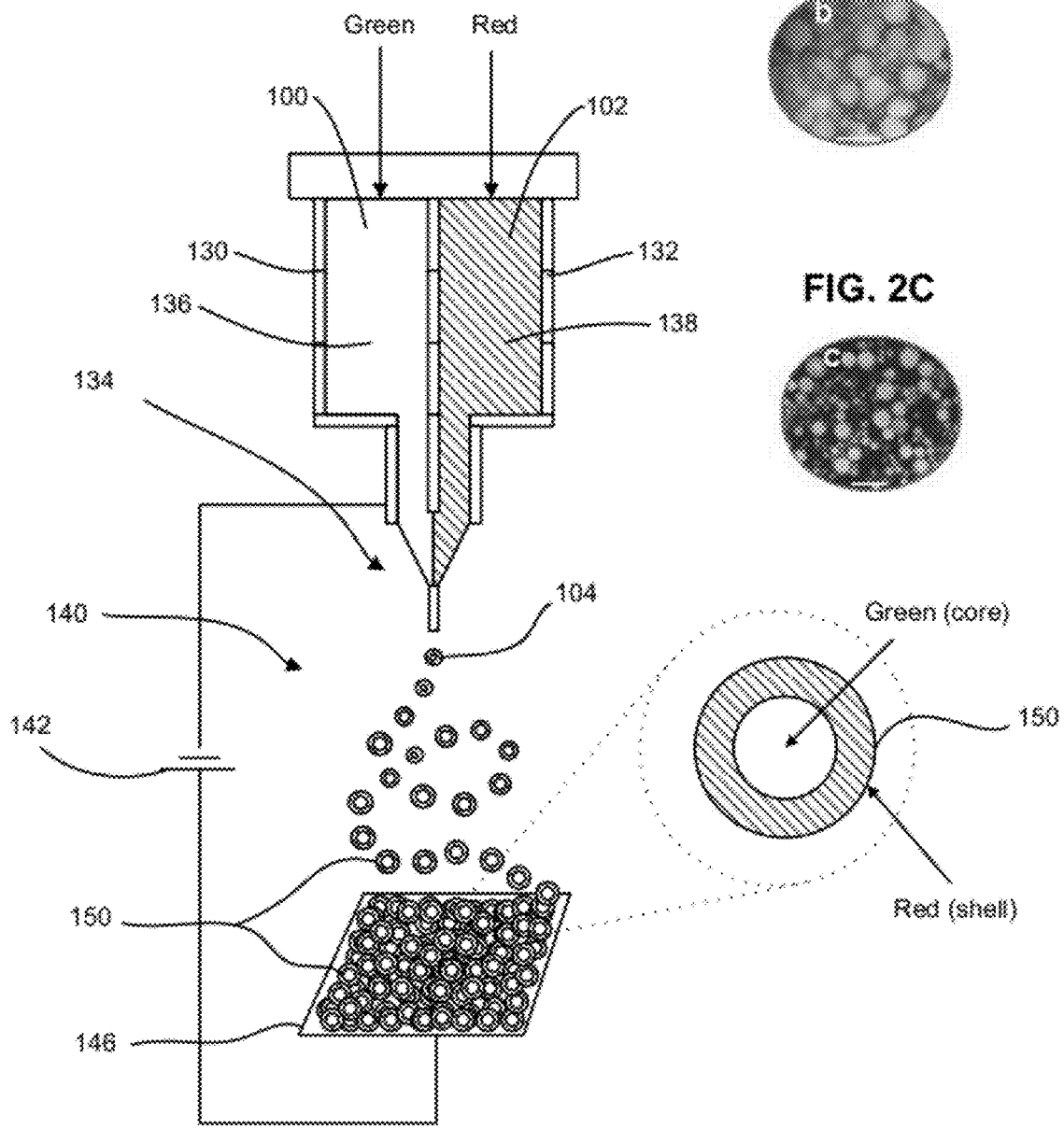
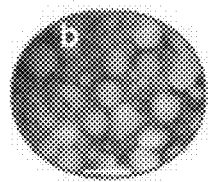
FIG. 2B
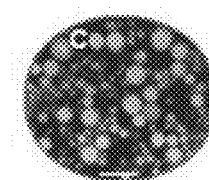
FIG. 2C
FIG. 2A

MICROPHASIC MICRO-COMPONENTS AND METHODS FOR CONTROLLING MORPHOLOGY VIA ELECTRIFIED JETTING

CROSS-REFERENCE TO RELATED APPLICATIONS

This application claims the benefit of U.S. Provisional Application No. 61/082,396, filed on Jul. 21, 2008.

This application is also a continuation-in-part of U.S. patent application Ser. No. 11/763,842 filed on Jun. 15, 2007, which published as U.S. Publication No. 2007/0237800, which is itself a continuation-in-part of U.S. patent application Ser. No. 11/272,194 filed on Nov. 10, 2005, which issued as U.S. Pat. No. 7,767,017, that claims priority to U.S. Provisional Application Nos. 60/626,792 filed on Nov. 10, 2004 and 60/651,288 filed on Feb. 9, 2005. U.S. patent application Ser. No. 11/763,842 filed on Jun. 15, 2007 also claims the benefit of U.S. Provisional Application No. 60/814,706 filed on Jun. 16, 2006.

The disclosures of each of the respective applications above are incorporated herein by reference in their respective entireties.

FIELD

The present disclosure relates to fabrication of micro and/or nano-particles and, more particularly, to methods of fabricating biodegradable multiphasic micro-components and/or nano-components.

BACKGROUND

The statements in this section merely provide background information related to the present disclosure and may not constitute prior art.

Nano-components and/or micro-components (e.g., particles having diameters between 10 nm and less than a few millimeters) are of increasing interest because of their potential applications as drug delivery systems, sensors, microreactors, combined imaging and therapeutics ("theranostics"), or food packaging materials, by way of non-limiting example. In particular, environmentally responsive particles, such as pH-responsive core-shell particles are desirable for their ability to produce custom-tailored release profiles. A series of conventional methods have been used to prepare core-shell particles including emulsion polymerization, layer-by-layer (LbL) adsorption onto solid particles, templated polymerization and template-assisted electropolymerization. However, such conventional fabrication methods tend to be expensive, time intensive, and typically require immiscible solutions, thus compositionally limiting the components formed.

In certain aspects, the present disclosure provides a method of controlling the morphology of a micro-component or nano-component formed via electrohydrodynamic formation techniques enabling a wide variety of composition via relatively facile formation of micro-components. The disclosure provides for the preparation of core-shell components or particles with well-defined structure (e.g., phase alignment) by a side-by-side co-jetting of polymer solutions. In accordance with the present disclosure, a series of methods can be used to prepare core-shell particles, using a layer-by-layer approach, pH-sensitive core-shell particles as well as hollow capsules can be prepared. Another approach to pH-sensitive core-shell particles is the assembly of macromolecules, which display pH-responsive properties, and undergo biodegradation.

SUMMARY

This section provides a general summary of the disclosure, and is not a comprehensive disclosure of its full scope or all of its features.

In various aspects, the present disclosure provides methods of forming multiphasic micro-components via an electrified jetting process. In certain aspects, the present disclosure provides a method of controlling the morphology of a multiphasic micro-component comprising providing a first liquid stream having a first electrical conductivity and comprising a first polyelectrolyte and a second liquid stream having a second electrical conductivity comprising a second polyelectrolyte. The first and second electrical conductivities are respectively selected to create a predetermined phase orientation in a solid micro-component. Then, at least a portion of the first liquid stream and at least a portion of the second stream are exposed to an electric force field sufficient to form the solid micro-component comprising a first phase and a second distinct phase. The first phase of the solid micro-component comprises material from the first liquid stream and the second phase comprises material from the second liquid stream, such that the first phase and the second phase are compositionally distinct from one another.

Thus, the first electrical conductivity and the second electrical conductivity in the first and second liquid streams are selected so as to create a predetermined phase orientation in the solid micro-component. By way of example, such a predetermined phase orientation may include substantially round micro-components having a core-shell phase alignment/morphology or an anisotropic phase alignment/morphology, where the first phase has a first exposed surface and the second phase has a second exposed surface.

In certain variations, an active ingredient can be introduced into the first or second streams and thereby forms a portion of the first phase or second phase in the solid micro-component. In other variations, after exposing the first and second streams to an electric force field, an active ingredient can be introduced into at least one of the first or second phases by contacting the active ingredient with a portion of the first or second phases for absorption therein. In certain aspects, the active ingredient may be absorbed by one or more phases. In certain variations, additional phases may be introduced into the micro-component by including additional liquid stream during exposure to the electric field.

In other aspects, the present disclosure provides multiphasic micro-components formed in accordance with such methods. For example, such methods enable use of similar compatible or miscible materials. In certain variations, a multiphasic micro-component comprises a first hydrophilic phase formed from a liquid stream comprising a first polyelectrolyte and a second hydrophilic phase formed from at least a portion of said core region formed from a distinct liquid stream comprising a second polyelectrolyte. The first hydrophilic phase and the second hydrophilic phase are compositionally distinct from one another. In certain aspects, at least one of the first and second phases comprises an active ingredient. Further, in certain aspects, the multiphasic micro-component optionally has a substantially round shape.

In yet other aspects, the present disclosure provides multiphasic core-shell micro-components comprising a first phase defining a core region formed from a liquid stream comprising a first polyelectrolyte and a second phase defining a shell region externally surrounding at least a portion of said core region formed from a distinct liquid stream comprising a second polyelectrolyte. The first and second phases are compositionally distinct from one another. At least one of the first and second phases comprises an active ingredient. Further, in certain variations, at least one of the first and second phases undergoes reversible swelling in response to an external stimulus from a surrounding environment.

Further areas of applicability will become apparent from the description provided herein. The description and specific examples in this summary are intended for purposes of illustration only and are not intended to limit the scope of the present disclosure.

DRAWINGS

The drawings described herein are for illustration purposes only and are not intended to limit the scope of the present disclosure in any way.

FIGS. 1A, 1B, and 1C depict multiphasic micro-components formed in accordance with the present disclosure having different phase alignments and respective volumes and surface areas of a first phase and a distinct second phase;

FIG. 2A shows an exemplary apparatus that forms multiphasic core-shell particles according to the present disclosure by electrically jetting liquid polymer streams in a side-by-side configuration;

FIG. 2B is a Scanning Electron Micrograph ("SEM") image of micro-spheres after jetting in a configuration shown in FIG. 2A, in accordance with the present teachings;

FIG. 2C is a confocal microscopy (CFM) image of micro-spheres after jetting in an apparatus configured as shown in FIG. 2A in accordance with the present teachings, indicating a core-shell structure has an average size distribution of (1.9+/−0.4)μm;

Figure 4:
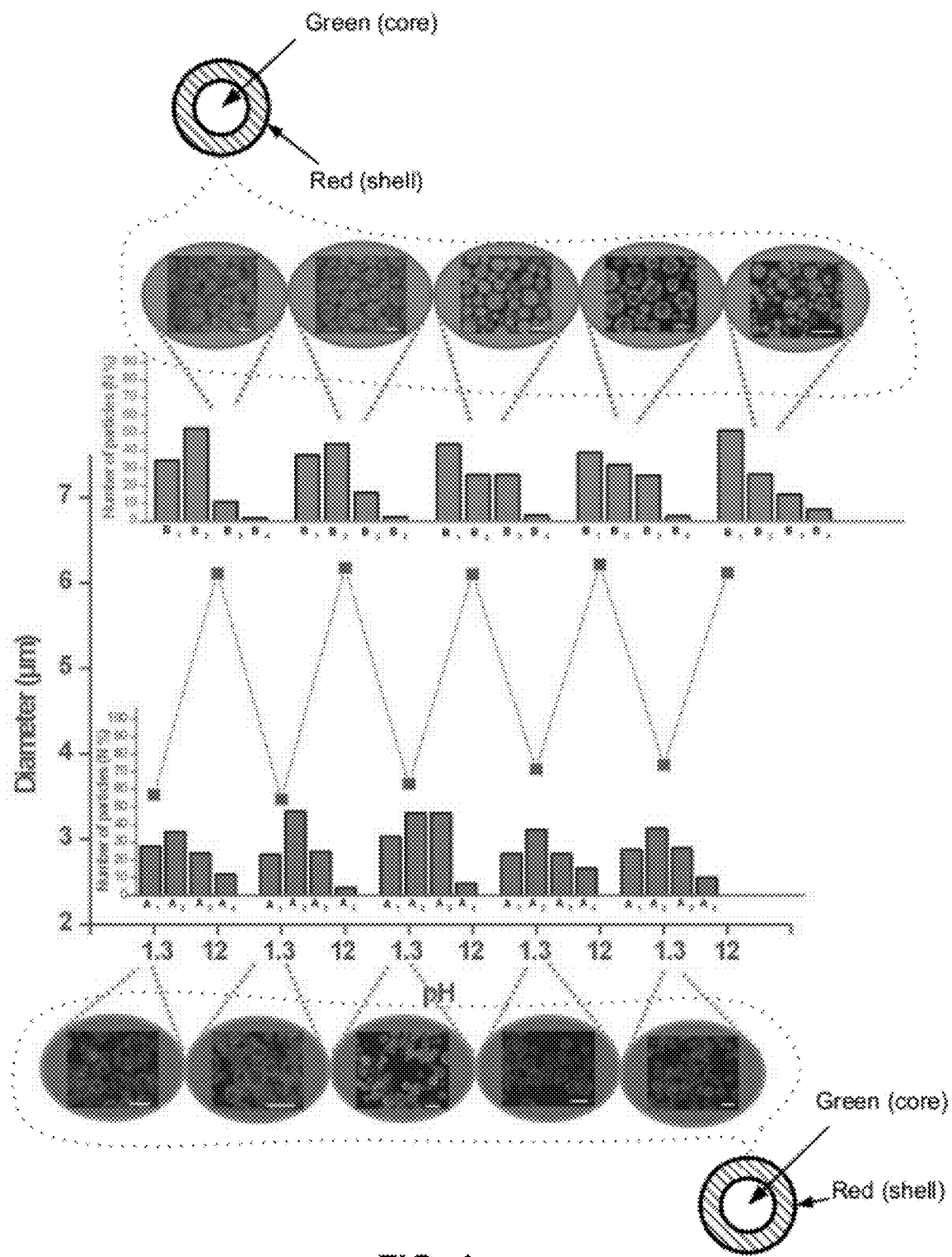
Figure 5:
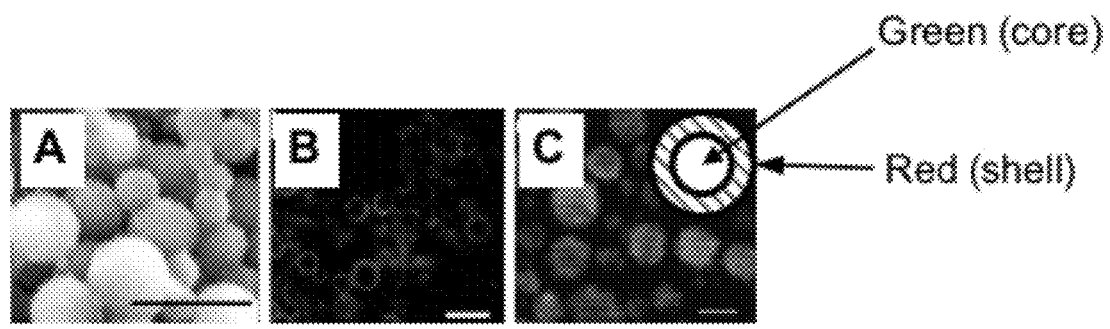
Figure 6:
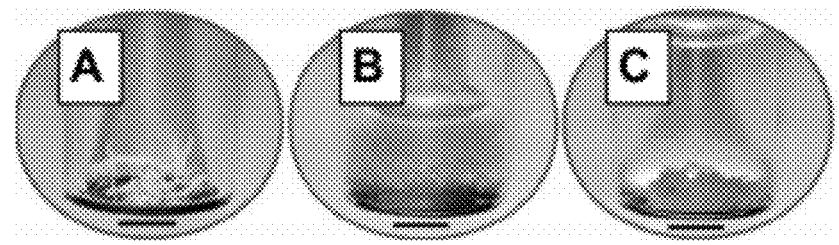
Figure 7:
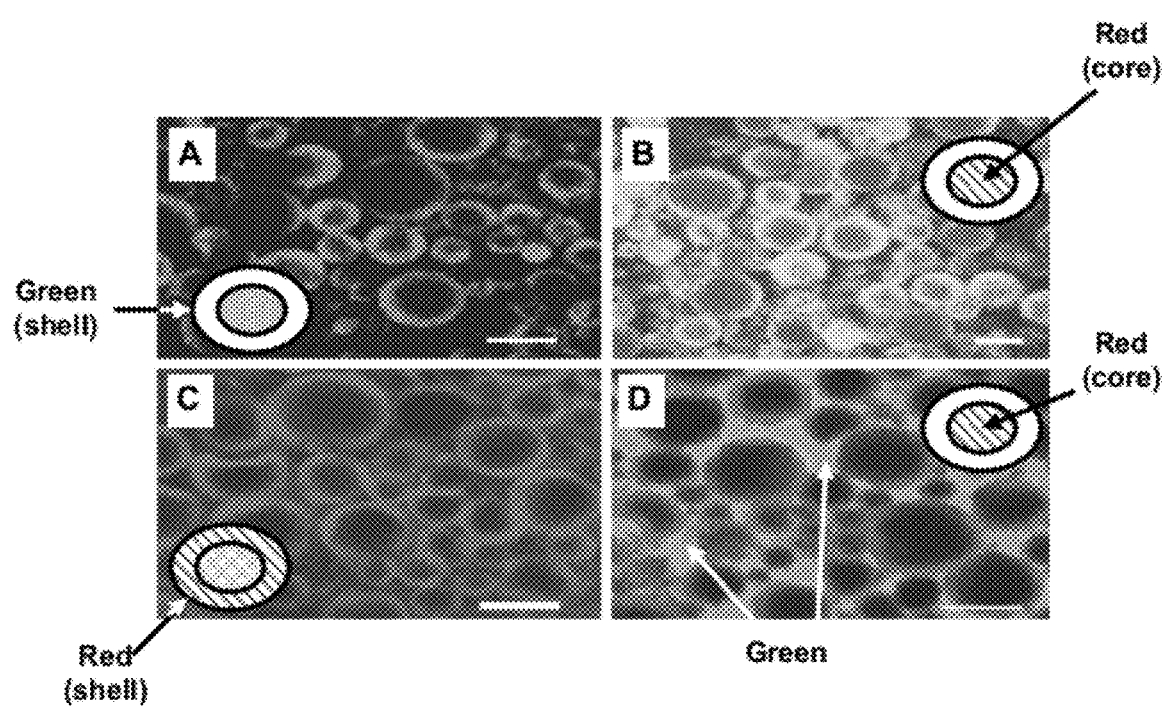
Figure 8:
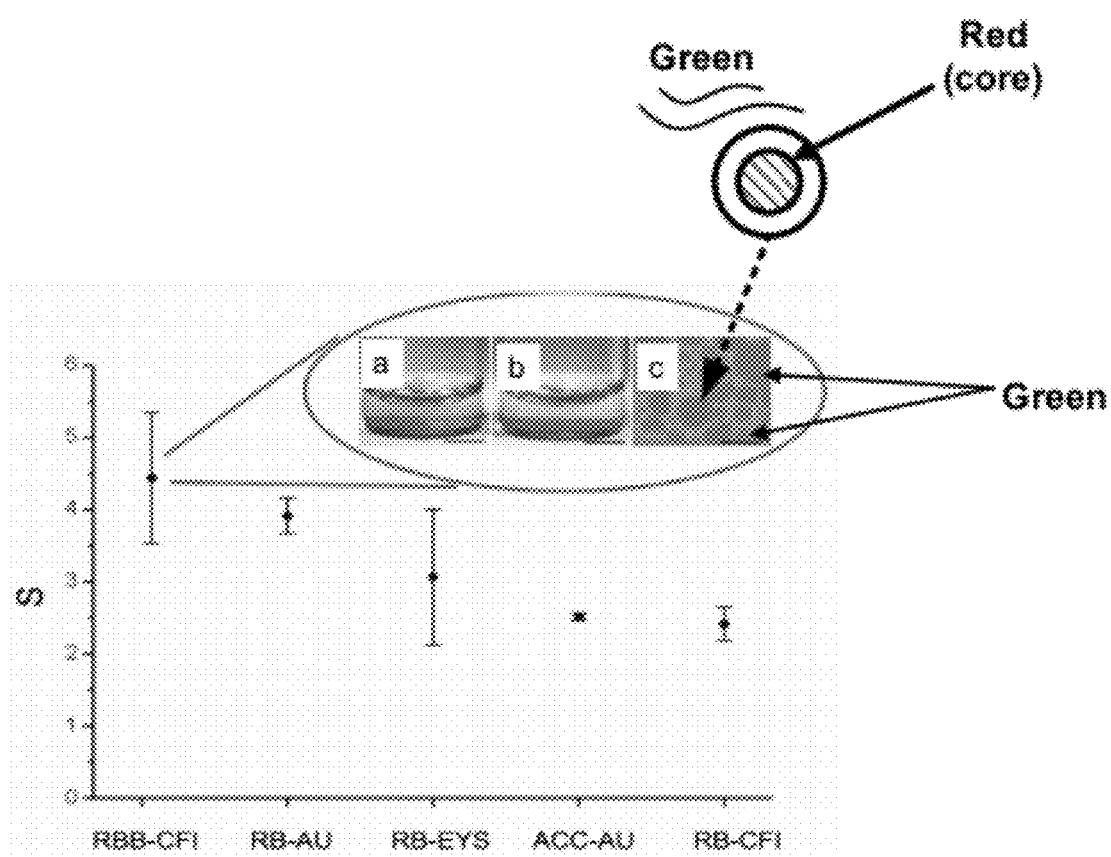

FIGS. 3A-3D are exemplary Scanning Electron Micrographs (SEM) of a spectrum of phase orientation morphologies formed according to the principles of the present disclosure, ranging from biphasic anisotropic Janus-type particles to core-shell particles, where morphology is controlled by using side-by-side co-jetting and controlling (e.g., increasing) the relative conductivity of the two polymer liquid jetting solution streams;

FIG. 4 shows the swelling behavior of (core-shell)$_{ab}$ particles when introduced to a media at pH 1.3 or 12 (using hydrogen chloride (HCl) or sodium hydroxide (NaOH) solutions in water). All scale bars represent 8 μm. Histograms indicate statistic calculations for size distribution of (core-shell)$_{ab}$ particles in acidic ($A_{index}$) or basic ($B_{index}$) environments in a given diameter range;

FIG. 5A is an exemplary SEM image of (core-shell)$_{ab}$ micro-component particles introduced to an acidic solution of pH 0.4 and dried in air;

FIG. 5B is an exemplary Confocal microscope (CFM) image of (core-shell)$_{ab}$ micro-component particles in the acidic media at (pH 0.4);

FIG. 5C is an exemplary Confocal microscope (CFM) image of (core-shell)$_{ab}$ particles after increasing pH of the media to 12 by adding NaOH solution to the media containing the particles at pH 0.4;

FIGS. 6A-6C are exemplary images of vials containing (core-shell)$_{ab}$ particles. FIG. 6A shows the (core-shell)$_{ab}$ particles after jetting in air in accordance with the present teachings, FIG. 6B shows the (core-shell)$_{ab}$ particles expanded in de-ionized water; and FIG. 6C shows (core-shell)$_{ab}$ particles contracted after exposure to a pH 0.4;

FIGS. 7A-7D are exemplary Confocal images (CFM) of various (core-shell)$_{a,b}$ particles formed in accordance with the principles of the present disclosure in different solutions, respectively; and FIG. 8 shows selective uptake of various compounds (distinct dye compounds) in multiphasic micro-component particles formed in accordance with the present disclosure.

DETAILED DESCRIPTION

The following description is merely exemplary in nature and is not intended to limit the present disclosure, application, or uses.

The present teachings provide a unique approach toward designing nano-carriers by enabling design of particles with multiple, distinct surface patterns or nano-compartments. In various aspects, the present disclosure provides methods of controlling the morphology and phase orientation of micro-components formed via electrojetting techniques. Because of its intrinsic simplicity and versatility, the electrohydrodynamic co-jetting process can be applied to a wide range of specialty and non-specialty materials. Since each phase or compartment can be designed independently from the other phase or compartment(s), the present disclosure provides for numerous combinations of multiple, essential material functions of micro-components.

A "micro-component" is a material that has a variety of shapes or morphologies, however, generally has at least one spatial dimension that is less than about 1,000 μm (1 mm), optionally less than 500 μm, optionally less than 250 μm, optionally less than 100 μm, optionally less than about 75 μm, optionally less than about 50 μm, optionally less than about 25 μm, optionally less than about 20 μm, optionally less than about 10 μm (i.e., 10,000 nm), and in certain aspects, optionally less than about 5 μm (i.e., 5,000 nm).

The term "micro-component" further includes "nano-sized" or "nanometer-sized," which are generally understood by those of skill in the art to mean less than about 10 μm (i.e., 10,000 nm), optionally less than about 2 μm (i.e., less than about 2,000 nm), optionally less than about 1 μm (i.e., less than about 1,000 nm), optionally less than about 0.5 μm (i.e., 500 nm), and in certain aspects, less than about 0.2 μm (i.e., 200 nm). In certain aspects, a micro-component as used herein has at least one spatial dimension that is greater than about 0.5 μm (i.e., 500 nm) and less than about 100 μm. In certain aspects, as used herein, a nano-component has at least one spatial dimension that is greater than about 1 nm and less than about 10,000 nm. In certain aspects, a nano-component has at least one spatial dimension of about 5 to about 5,000 nm. In some aspects, at least one spatial dimension of the nano-component is about 20 to about 2,000 nm. In still other variations, nano-components have at least one spatial dimension of about 50 to about 500 nm.

In various aspects, the present teachings provide methods of forming micro-components having well-defined structures, particularly suitable for forming substantially round shaped micro-components. In certain embodiments, these substantially round-shaped micro-components can be capsules to deliver active ingredients to a target. "Substantially round-shaped" includes micro-components having a morphology or shape including spherical, spheroidal, hemispherical, disk, globular, annular, toroidal, cylindrical, discoid, domical, egg-shaped, elliptical, orbed, oval, and the like. In certain aspects, the present teachings provide the ability to select not only the micro-component morphology, but also a predetermined orientation of respective phases within the micro-component, as described in more detail herein. In other aspects, the present teachings may further be used to form other solid micro-components morphologies, such rectangles, polygons, cones, pyramids, rods, beads-on-a-string, and/or fibers, by way of non-limiting example.

Thus, in various aspects, the multiphasic micro-components according to the present teachings include a first phase and at least one additional phase that is distinct from the first phase. In certain aspects, the multiphasic components of the present disclosure include multiple distinct phases, for example three or more distinct phases. As used herein, "multiphase" or "multiphasic" means that at least two phases herein occupy separate but distinct physical spaces to form the micro-component shape. In certain embodiments, such phases are in direct contact with one another (e.g., they are not separated by a barrier and they are not emulsified or mixed to any significant degree). By the term "phase" it is meant that a portion, domain, or region of a component is chemically and/or physically distinct from another portion, domain, or region of the component, for example a phase may have one average composition distinct from another phase having a different average composition. Each respective phase optionally occupies a spatially discrete region or compartment of the nano-component.

In certain embodiments, the multiphasic micro-components are anisotropic. For example, in certain variations, a substantially round multiphasic micro-component may have an anisotropic morphology, where each respective phase of the multiphasic component is exposed to an external environment, thus providing a different composition in different directions of the micro-component. Biphasic particles having such a side-by-side anisotropic phase orientation are often referred to as a "Janus particle"; however the present teachings encompass various anisotropic multi-phasic particles, where each respective phase has an externally exposed surface. The exposure of each respective surface of each phase provides enhanced environmental interface. Other morphologies include isotropic or concentric morphologies. For example, a substantially round multiphasic micro-component may have a core-and-shell morphology (or "core-shell"), where one or more phases occupy a core region and one or more phases externally surround at least a portion of the core region.

Configurations such as those shown in FIGS. 1A and 1B have three phase interfaces. In FIG. 1A, a first phase 20 and a second phase 22 share a first phase interface 26, where both the first phase 20 and second phase 22 occupy discrete spatial locations within the micro-component. First phase 20 also interacts with an external environmental medium 28 at a second phase interface 30. Lastly, the second phase 22 has a third phase interface with the medium 30 at a third phase interface 32. The micro-component has a phase alignment/morphology that is thus anisotropic, wherein first phase 20 has an exposed surface at second phase interface 30 and second phase 22 has an exposed surface at third phase interface 32. In FIG. 1B, a first phase 20' has a reduced surface area that is exposed to external medium 28 than the second phase 22'. However, such phases 20, 22' have a first, second, and third phase interface 26', 30', 32', like in FIG. 1A.

In another variation, the multiphasic micro-component may have a core and shell configuration, as shown in FIG. 1C. Such a configuration only has two phase interfaces between a first phase 40 and a second phase 42. A first phase interface 44 between the first phase 40 and second phase 42 and a second phase interface 46 between second phase 42 and an external medium 48. Thus, the first phase 40 defines a core region and second phase 42 defines at least a portion of a shell region. Notably, in certain alternate embodiments, the shell region may surround only a portion of the core region, rather than fully enclosing the core region.

It has previously been a particular challenge to form core-shell morphologies having similar materials in both the core region and the shell region. For example, conventional methods have not been able to form core-and-shell morphology micro-components comprising a hydrophilic material in the core region and a distinct hydrophilic material in a shell region. Electrohydrodynamic co-jetting can be used to prepare biphasic and triphasic nano-colloids, i.e., solid particles with multiple compartments or distinct phases. Furthermore, in the context of electrohydrodynamic co-jetting processes, forming a core-shell morphology via a side-by-side co-jetting of polymer solutions (rather than a concentric set-up, where a first stream is jetted inside a surrounding external stream) has been particularly difficult. However, the teachings of the present disclosure provide the ability to optionally form core-shell morphology micro-components, optionally having similar materials, in both the core and shell phases, for example, a hydrophilic phase defining the core region and a hydrophilic phase defining the shell region.

Thus, the present methods form such core-shell micro-components via a side-by-side jetting configuration without the need to specially adapt the configuration of needles of electrohydrodynamic jetting apparatus to create coaxial liquid streams. Instead, by selection of certain material properties for the liquid streams, the present methods create a predetermined phase orientation in the solid micro-components, including core-in-shell morphology, without any need to modify the electrohydrodynamic jetting apparatus set-up.

For example, in certain aspects, the present methods include forming a composite stream by contacting a portion of a first liquid stream having a first electrical conductivity with a portion of a second liquid stream having a second electrical conductivity. At least a portion of the composite stream is exposed to an electric force field sufficient to form a solid micro-component having a core-shell morphology, which comprises a first phase and a second distinct phase. A difference between the first electrical conductivity of the first liquid stream and a second electrical conductivity of a second liquid stream ($\sigma_1$-$\sigma_2$=$\Delta\sigma$) controls the phase orientation in the micro-component. Thus, in accordance with the present teachings the micro-component is designed to have a predetermined phase orientation and morphology, such as a core-shell morphology, can be selected based upon tailoring the properties of the respective liquid streams, like electrical conductivity. In certain aspects, energy (e.g., thermal energy, actinic or UV radiation, or electron beam energy) is applied to the micro-component after exposing it to the electric field to cure at least one polymer in the micro-component.

In various aspects, the multiphasic micro-components are formed by electrified jetting of materials that comprise one or more polymers, such as that disclosed by Roh et al. in "Biphasic Janus Particles With Nanoscale Anisotropy", Nature Materials, Vol. 4, pp. 759-763 (October, 2005), as well as in U.S. application Ser. No. 11/763,842 filed on Jun. 15, 2007 entitled "Multiphasic Biofunctional Nano-components and Methods for Use Thereof," U.S. application Ser. No. 11/272,194 filed on Nov. 10, 2005 entitled "Multiphasic Nanoparticles," and in U.S. Provisional Patent Application Nos. 60/626,792 filed on Nov. 10, 2004 and 60/651,288 filed on Feb. 9, 2005, all of which are to Lahann et al. The contents of each of these respective references are hereby incorporated by reference in their respective entireties.

As demonstrated by FIG. 2A, a simplified electrified jetting system is shown that develops liquid jets having a micrometer-sized or nanometer-sized diameters, using electro-hydrodynamic forces. A "side-by-side" configuration of Fluids A 100 and B 102 are combined to form a pendant droplet 104 of conducting liquid. The drop 104 is exposed to an electric potential of a few kilovolts, where the force balance between electric field and surface tension causes the meniscus of the pendent droplet 104 to develop a conical shape, the so-called Taylor cone (not shown). Above a critical point, a highly charged liquid jet is ejected from an apex of the cone. This well-established process has been employed by two processes, i) electrospraying and ii) electrospinning.

In electrospraying, the ejected liquid jet is eventually fragmented due to instabilities and forms a spray of droplets. Among the various applications, production of charged gas phase ions of bio-macromolecules for mass spectroscopy is the most widely used. Using polymer solutions or melts as jetting liquids, electrospinning gives a way to develop fibers whose diameters are a few orders of magnitude smaller than those available from conventional spinning. Electrospinning can employ a wide variety of polymers, as are generally known in the art.

With renewed reference to FIG. 2A, the exemplary electrojetting apparatus has two jetting liquids 100, 102 combined to form a multi-phasic micro-component particle 150. In order to incorporate two different streams into each side of a composite stream, channels 130, 132 are configured adjacent to each other (i.e., side by side) in nozzle 134. In some variations, channels 130, 132 are capillaries. Channels 130, 132 feed two different jetting liquid streams 100, 102 into region 140 having an electric field generated by power supply 142. Channels 130, 132 are of sufficient dimensions to allow contacting of liquids streams 100, 102 to form the composite stream. In one variation, this electric field is generated by the potential difference between nozzle 134 and plate 146. Typically, an electric field is formed by applying a potential difference between at least two electrodes from about 0.1 kV to about 25 kV. Various configurations of plates and geometries may be used to generate the electric field as known to those of skill in the art and are contemplated by the present disclosure.

FIG. 2A illustrates the electrospraying method of forming multiphasic micro-components in which particles 150 are formed. In this variation, the ejected composite stream from nozzle 134 is fragmented due to instabilities thereby forming a spray of droplets.

Morphological control can be achieved in accordance with the present teachings with the exemplary electric jetting formation methods described herein. Therefore, the composite liquid stream, which is ejected from a pendant cone at the nozzle 134, is fragmented to small droplets. The size and/or diameter of the droplet 134 can also be controlled. Such control is attained by changing either the material properties of jetting liquids or the working parameters of electrified jetting that breaks-up the jet stream. It should be appreciated, however, that the final morphology of the liquid jet is not always the same as those of the solid products collected on the substrates. The shape of final products can also be controlled by a sol-gel transition process or by subsequent processing after formation by electric jetting. In certain aspects, multiphasic micro-components use a sol-gel transition intrinsically in the process, since the jetting liquids are polymer solutions or polymer melts, and solvent evaporation or a temperature drop below the thermal transition temperature during the jetting acts as a sol-gel treatment step.

Since the electrified jetting methods are related to electro-hydrodynamic processes, the properties of the jetting liquid and operating parameters are interrelated. Moreover, when the jetting liquids are not one-component systems (i.e., mixtures of two or more compounds), the jetting liquid is a solution having properties governed by several parameters of the solvent and solutes. It should be appreciated that liquid properties, solution parameters, and operating parameters are related, as recognized by those of skill in the art. Relevant material properties include viscosity, surface tension, volatility, thermal and electrical conductivity, dielectric permittivity, and density.

Where the two polymer solutions are compatible with one another, a stable cone-jet forms a stable interface between the two phases. In such situations, it is believed that the process is kinetically controlled (rather than thermodynamically controlled), resulting in one phase being trapped in each side before it mixes with the other phase. In other embodiments, the two phases, i.e., the two jetting liquids (or solutions) are optionally incompatible with each other (e.g., immiscible or insoluble). The present disclosure further contemplates multiple phases (in excess of two), which may be respectively compatible or incompatible with one another, that form multiphasic particles via electrified jetting processes.

During electrified jetting processes, relevant solution properties include concentrations, molecular weight, solvent mixtures, surfactants, doping agent, and cross-linking agents. Relevant operating parameters include flow rate of the liquid streams, electric potential, temperature, humidity, and ambient pressure. With regard to the operating parameters, the average size and size distributions of the droplets in electrospraying with cone-jet mode appear to be dependent on the flow rate (pumping rate of the jetting liquids). At a fixed flow rate, one or several relatively monodisperse classes of nano-component diameters are formed. At minimum flow rate, the modality of the distributions and diameter of the droplet itself also show their minima. When the flow rate is changed, the electric field can be adjusted by changing either distance or electric potential between the electrodes in order to sustain a stable cone-jet mode. Higher flow rates may be accompanied by a higher electrical field applied for mass balance of jetting liquids. When the diameter of droplets is larger than desired, solvent evaporation does not fully occur before the droplets reach the collecting substrate, so the resulting droplets may be wet and flat.

Thus, electrohydrodynamic jetting is a rather complex process and the ultimate particle geometry depends on a variety of parameters, which may be classified as materials-related or process-related factors. Important materials-related parameters in accordance with the present teachings include viscosity, electrical conductivity, and/or free surface energy of the jetting solutions, while process-related parameters include the magnitude of the applied electric field, solution flow rates, nozzle geometry, and temperature. In case of certain embodiments described herein, the materials-related parameters are independently controlled for each polymer solution, while most of the process-related factors are not independently controlled for electro-hydrodynamic co-jetting.

In various aspects, the use of the electric jetting methods of the disclosure provide greater control over the morphology and design of the nano-components as opposed to other methods of forming nano-components (such as sonication during liquid jetting and the like). For example, the liquid jetting in the presence of an electric field of the present disclosure permits the use of immiscible materials as the first and second phases, as well as miscible materials. The broad use of such materials is possible due to the rapidity of formation of particles and shapes when an electric field is applied. For many conventional methods of formation, the respective phases require immiscibility between the phases; however that is not a requirement with the electric jetting methods of the present technology. Further, the methods of forming the multiphasic micro-components by use of side-by-side electric jetting further provides a high degree of control over the ability to create a wide variety of shapes, including substantially round shaped anisotropic multiphasic (e.g., Janus) particles or core-shell particles.

As noted above, in accordance with the present technology, electrical conductivity of the respective streams, more particularly the difference in electrical conductivity between the respective streams, is particularly important when controlling particle morphology and phase orientation. In various aspects of the present teachings, a first electrical conductivity of a first liquid jetting stream and a second electrical conductivity of a second liquid jetting stream are selected to create a predetermined phase orientation in said solid micro-component.

While not limiting the present disclosure to any particular theory, it is believed that the difference in the resultant phase alignment/geometry for substantially round-shaped multiphasic micro-components is due to electrical conductivity difference between respective jetting solutions (e.g., polymer solution). As schematically presented in FIGS. 3A-3D, the biphasic jet which is ejected by the stable biphasic cone can be either fragmented with predetermined phase orientation within the micro-component. The predetermined phase orientation is achieved by selecting certain properties of the liquid stream compositions that form the phases of the micro-component, for example, the electrical conductivities. The impact of selecting electrical conductivity for respective jetted liquid streams is shown in FIGS. 3A-3D.

In FIGS. 3A-3D, the two phases, i.e., the two jetting liquids (or solutions) are compatible with each other (e.g., miscible or soluble). In contrast to many of the existing methods of particle fabrication, such as emulsion polymerization, this approach does not require use of immiscible solutions. When the liquid jetting compositions that form the phases of the micro-component have respective electrical conductivities that are similar or the same as one another, the biphasic nano-droplets formed are an anisotropic multiphasic (e.g., Janus) particle (where each phase has a respective exposed surface). Alternately, the predetermined phase orientation may be a shell-and-core morphology when the liquid jetting compositions that form the phases of the micro-component have a mismatch or difference between respective electrical conductivities, for example (where one or more phases define a core region within another shell phase as in FIG. 3D).

Figure 3:
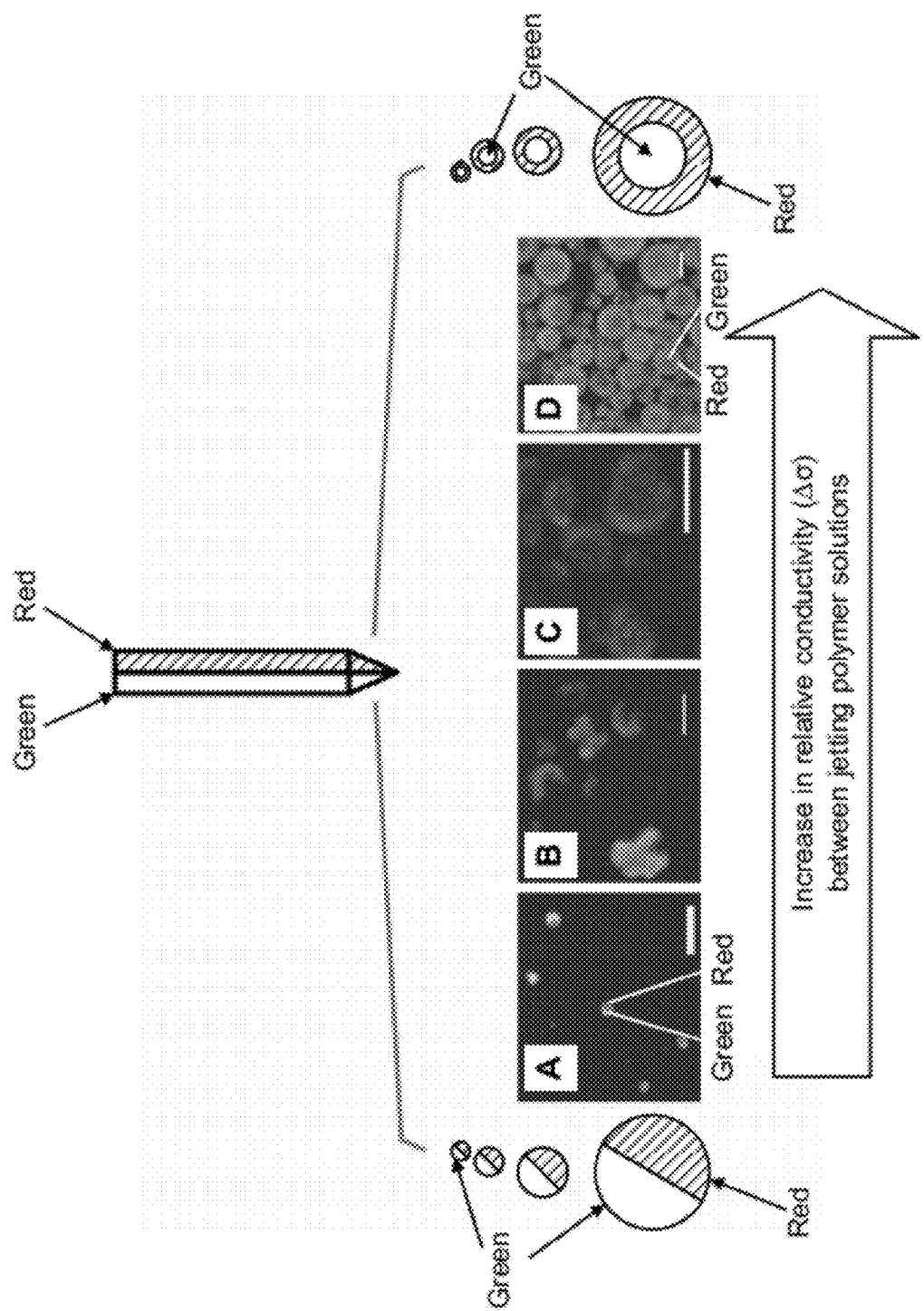

Electrohydrodynamic jetting relies on the creation of surface charges during the acceleration of polymer solutions in the high electrical field between the conductive needle and the counter electrode. In principle, the electrohydrodynamic co-jetting process is compatible with a range of different polymer solutions, including aqueous and organic solutions, which can be associated with a range of different conductivities. If polymer solutions with significantly different conductivities are co-jetted, each phase of the droplet accelerates unevenly towards the counter electrode. Solutions with lower conductivity typically yield higher jet velocities due to higher interfacial charge build-up. In a simplified model for electrohydrodynamic co-jetting of two solutions with distinct conductivities, the solution with lower conductivity functions as the lead phase. The lead phase is initially accelerated, but immediately creates a viscous drag on the second solution, which is pulled along and may be considered a dependent phase. In FIG. 3D, the less conductive lead phase is indicated at 20, forming the shell of the resultant particles, while the dependent phase 22 tends to form the core.

This technology enables control of multiphasic micro-component architecture, for example, to form core-shell phase orientation without having any change of the position (geometry) of the jetting set up or configuration, which is an easy approach to production of the core-shell particles with a well-defined structure.

In various aspects of the present teachings, the multiphasic components comprise at least one polyelectrolyte. As used herein, a polyelectrolyte is a polymeric macromolecule in which a substantial portion of the constitutional units (e.g., monomers) contain ionic or ionizable groups, or both. In accordance with the present methods, a liquid stream comprises at least one polyelectrolyte that is electrically jetted and forms the material of the first phase, which may be further cross-linked or treated. Thus, each phase of the multiphasic micro-component may comprise a polyelectrolyte or a subsequent product thereof. While each respective liquid stream must be compositionally distinct from the others, in certain aspects, for each liquid stream may be selected to include the same polyelectrolyte, albeit optionally at the same or different concentrations, as other components may be present in certain phases. In other aspects, each liquid stream may comprise two or more of the same polyelectrolytes, optionally at the same or different concentrations. In yet other aspects, each liquid stream may comprise distinct polyelectrolytes.

Suitable polyelectrolytes for use in the methods of the present disclosure are hydrophilic and synthetic or of non-biologic origin. By way of non-limiting example, examples of suitable polyelectrolytes include sulfonic acid based co-polymers, such as poly(vinyl sulfonic acid) (PVS) or sodium polystyrene sulfonate (PSS), and carboxylic acid based co-polymers, such acrylic or methacrylic acid based polymers, such as poly(acrylic acid) (PAA); acrylic acid-acrylate copolymers; acrylic acid-acrylamide copolymers, like poly (acrylamide acrylic acid) (PAAm) and poly(acrylamide-co-acrylic acid) ((PAAm-co-AA)—also referred to as PAAm-AA); acrylamide-sulfonic acid copolymers (2-acrylamido-2-methyl-1-propane sulfonic acid (APSA)), acrylic acid-olefin copolymers; acrylic acid-vinyl aromatic copolymers; acrylic acid-styrene sulfonic acid copolymers; acrylic acid-vinyl ether copolymers; acrylic acid vinyl acetate copolymers; acrylic acid-vinyl alcohol copolymers; polymers of methacrylic acid (e.g., polymethyl methacrylates (PMMA)) or copolymers of methacrylic acid with any of the above monomers; copolymers of maleic acid, fumaric acid and their esters with all of the above with all of the above monomers/co-monomers; copolymers of maleic anhydride with all of the above monomers/co-monomers; and the salt forms of all of the above.

Other polymers well-suited for use as polyelectrolytes in accordance with the present teachings include those having ammonium groups, such as quaternary ammonium groups, or amine groups. One example of such a polyelectrolyte includes polyethylene imine (PEI). In other aspects, polymers that include weak or strong acid groups, such as sulfate, sulfonate, phosphate, phosphonate, and/or carboxylate, are suitable polymers as polyelectrolytes. In particular, in certain aspects such polymer polyelectrolytes facilitate formation of core-shell particles. In yet another embodiment, polymers that include zwitter-ionic groups, i.e., having both positively and negatively charged groups in the same polymeric monomer or entity, are likewise suitable for use as polyelectrolytes, in particular, for formation of core/shell particles. In certain alternate aspects, suitable polyelectrolytes may include natural or synthetic polypeptides, which include chains of peptides (amino acids linked via peptide bonds) that may include without limitation charged amino acid groups, such as arginine, asparagine, aspartic acid, glutamic acid, glutamine, histidine, lysine, serine, threonine, and/or tyrosine, and the like. In yet other aspects, blends and mixtures of any of the above mentioned polymers may be used as suitable polyelectrolytes to form multiphasic micro-particles having a predetermined phase geometry, such as core/shell micro-components.

In certain variations, a first polyelectrolyte and a second polyelectrolyte are independently selected from the group consisting of: polyacrylic acid (PAA), poly(acrylamide acrylic acid (PAAm), and/or poly(acryl amide-co-acrylic acid) (PAAm-AA), sodium polystyrene sulfonate (PSS), polyethylene imine (PEI), polypeptides, copolymers, and combinations thereof. In certain preferred aspects, a first polyelectrolyte and a second polyelectrolyte are independently selected from the group consisting of: polyacrylic acid (PAA), poly(acrylamide acrylic acid (PAAm), and/or poly (acryl amide-co-acrylic acid) (PAAm-AA), sodium polystyrene sulfonate (PSS), copolymers, and combinations thereof.

Thus, in certain aspects, polyelectrolyte solutions used for jetting of the particles are optionally solutions of poly(acrylic acid) (PAA), poly(acrylamide acrylic acid) (PAAm), poly (acrylamide acrylic acid) (PAAm), and/or poly(acrylamide-co-acrylic acid) (PAAm-co-AA—also referred to as PAAm-AA).

In certain embodiments, a combination of PAAm-AA and PAA polyelectrolytes are used, and a ratio of PAAm-AA to PAA differs for each respective phase. For example, a ratio of PAAm-AA to PAA may vary in a first phase forming a core region and a second phase forming at least a portion of a shell region.

In certain aspects, multiple phases of the multiphasic micro-components optionally comprise one or more polymers in addition to the polyelectrolytes discussed above. In certain aspects, the polymers, including polyelectrolytes, can also be modified by chemical or physical methods, such as cross-linking, heat treatment, photochemical treatment, and/or changes in the chemical or physical environment. In yet other aspects, the polymer modification occurs in a select portion or region of one or more of the multiple phases, or such polymer modification can occur to different degrees, potentially resulting in different materials or materials responses, as appreciated by those of skill in the art. Such polymer modification and/or treatment provide different release kinetics in certain embodiments for the multiphasic micro-components.

Other exemplary polymers for use in the micro-components formed in accordance with the present teachings include biocompatible polymers, biodegradable or non-biodegradable polymers (in addition to the polyelectrolyte polymers discussed above), or natural polymers. In certain respects, different polymers used in the different phases of the multiphasic micro-components permit different active ingredient release kinetics, which can be useful in designing release of the active ingredient into the environment.

Other suitable polymers for use in the micro-component particles formed in accordance with the present teachings include polyethers, polyethylene oxide (PEO), poly α-hydroxy acids polyester polymers, such as polylactic acid (poly (lactide)), polycaprolactone, polyglycolic acid (poly(glycolide)), poly(lactide-co-glycolide) polymer (PLGA), poly (dioxanone), poly(capralactone), poly(3-hydroxybutyrate), poly(3-hydroxyvalerate), poly(valerolactone), poly(tartronic acid), poly (β-malonic acid), poly[lactide-co-(propargyl glycolide hydroxy alkyl cellulose polymers, hydroxypropyl methyl cellulose (HPMC), hydroxypropyl cellulose (HPC), hydroxyethyl cellulose (HEC), methyl cellulose (MC), carboxymethyl cellulose (CMC), vinyl acetate, polyvinylpyrrolidone (PVP), polyvinylpyrrolidone-vinyl acetate copolymers, polyvinyl alcohol (PVA), vinyl acetate, crotonic acid copolymer, polyacrylamide, polyethylene phosphonate, polybutene phosphonate, polystyrenes, polyvinylphosphonates, polyalkylenes, carboxy vinyl polymer, cellulose acetate, cellulose nitrate, ethylene-vinyl acetate copolymers, vinyl acetate homopolymers, ethyl cellulose, butyl cellulose, isopropyl cellulose, shellac, siloxanes, polydimethylsiloxanes, cellulose acetate phthalate, natural or synthetic rubber; cellulose, polyethylene, polypropylene, polyesters, polyurethane, nylon, poly(aryleneethynylenes) (PAE), polythiophene, polyaniline, poly(p-phenylene), poly(p-phenyleneethynylene) (PPE), poly(p-phenylenevinylene), copolymers, derivatives, and mixtures thereof.

Thus, in certain embodiments, the phases of the multiphasic micro-components dissolve or disintegrate at different rates. In this regard, the dissolution rate of the respective phases impacts the release rate of an active ingredient that may be present in each phase, thus providing control over the release kinetics and concentration of active ingredient to be delivered to target regions with each respective phase of the nano-component. As referred to herein, "dissolve" refers to physical disintegration, erosion, disruption and/or dissolution of a material. The phases may dissolve or disintegrate at different rates or have different solubility (e.g., aqueous solubility) that impacts the rate of active ingredient release. Each phase comprises one or more materials that dissolve or erode upon exposure to a solvent comprising a high concentration of water, such as serum, blood, bodily fluids, or saliva. In some variations, a phase may disintegrate into small pieces or may disintegrate to collectively form a colloid or gel.

In certain variations, a phase of the multiphasic micro-component comprises a polymer that is insoluble or has limited solubility in water, but is dispersible in water, so that the polymer breaks down or erodes into small fragments. In other aspects, a polymer used in a phase of the multiphasic micro-component is insoluble in water, but is swellable. In variations where a polymer does not fully break down during use, the polymer can be a water-repellant polymer or an aqueous-stable hydrophilic polymer, for example, certain types of cellulose. In various aspects, each phase of the multiphasic micro-components optionally comprises a combination of polymer materials.

Water-soluble and/or hydrophilic polymers, which are cosmetically and pharmaceutically acceptable, include polyelectrolytes, such as acrylates and polyacrylic acid (PAA), including polyacrylate polymer, vinylcaprolactam/sodium acrylate polymers, methacrylates, poly(acryl amide-co-acrylic acid) (PAAm-co-AA), by way of non-limiting example. Other suitable water-soluble and/or hydrophilic polymers include cellulose ether polymers, such as those selected from the group consisting of hydroxyl alkyl cellulose, including hydroxypropyl methyl cellulose (HPMC), hydroxypropyl cellulose (HPC), hydroxyethyl cellulose (HEC), methyl cellulose (MC), carboxymethyl cellulose (CMC), and combinations thereof. Yet other cosmetically and pharmaceutically acceptable polymers among those useful herein include polyvinylpyrrolidone, vinyl acetate, polyvinylpyrrolidone-vinyl acetate copolymers, polyvinyl alcohol (PVA), vinyl acetate and crotonic acid copolymers, polyacrylamide, polyethylene phosphonate, polybutene phosphonate, polystyrene, polyvinylphosphonates, polyalkylenes, and carboxy vinyl polymers. The multiphasic compositions may comprise derivatives, copolymers, and further combinations of such polymers, as well.

Other cosmetically and pharmaceutically acceptable water-soluble polymers or fillers among those useful herein include, without limitation, sodium alginate, carrageenan, xanthan gum, gum acacia, Arabic gum, guar gum, pullulan, agar, chitin, chitosan, pectin, karaya gum, locust bean gum, various polysaccharides; starches such as maltodextrin, amylose, corn starch, potato starch, rice starch, tapioca starch, pea starch, sweet potato starch, barley starch, wheat starch, modified starch (e.g., hydroxypropylated high amylose starch), dextrin, levan, elsinan and gluten; and proteins such as collagen, whey protein isolate, casein, milk protein, soy protein, keratin, gelatin, and combinations thereof.

Further, non-limiting examples of cosmetically and pharmaceutically acceptable water insoluble or hydrophobic polymers known in the art, include cellulose, cellulose acetate, cellulose acetate phthalate, cellulose nitrate, ethylene-vinyl acetate copolymers, vinyl acetate homopolymer, ethyl cellulose, butyl cellulose, isopropyl cellulose, shellac, siloxanes, such as hydrophobic silicone polymer (e.g., poly (dimethylsiloxane) (PMDS)), poly(methyl methacrylate) (PMMA), natural or synthetic rubbers; polyethylene, polypropylene, polyesters, polyurethane, nylon, and copolymers, derivatives, and combinations thereof. The polymers may be crosslinked after formation by application of heat, actinic radiation or other methods of curing and treating polymers known to those of skill in the art.

In certain variations, a crosslinking reaction is carried out in order to prevent dissolution of the phases (for example, in a solvent) and to optionally provide control over swelling behavior of the particles in aqueous-based fluids. Thus, a cross-linking agent, such as a cross-linkable monomer or oligomer (which may be a polyelectrolyte or may be an additional component added to the liquid stream that forms a phase). In certain aspects, a crosslinking reaction occurs between free amide and carboxylic functional groups in the polyelectrolytes. With certain material systems, such as those where a polymer is a polyelectrolyte, such as PAA, PAAm, and/or PAAm-AA, a cross-linking reaction can desirably provide the ability for one or more phases to reversibly swell in response to external stimuli, as will be described in more detail below.

In order to further modify the conductivity of one or more of the phases, the pH can be modified by incorporating a pH modifying agent or buffering agent into one of the jetting solution compositions. For example, in certain embodiments, a liquid jetting composition that defines a core region of the micro-components after jetting may be altered by including such a pH altering agent or buffering agent to increase electrical conductivity. Such agents include acidifying agents to lower pH, basifying agents to raise pH and buffering agents to control pH within a desired range. For example, one or more compounds selected from acidifying, basifying and buffering agents can be included to provide a pH of about 2 to about 12, or in various illustrative embodiments about 2 to about 10, and the like. Exemplary and non-limiting pH modifying agents can be used, including without limitation carboxylic, phosphoric and sulfonic acids, acid salts (e.g., monosodium citrate, disodium citrate, monosodium malate, etc.), alkali metal hydroxides such as sodium hydroxide (NaOH), carbonates such as sodium carbonate, bicarbonates, sesquicarbonates, borates, silicates, phosphates (e.g., monosodium phosphate, trisodium phosphate, pyrophosphate salts, etc.), imidazole and the like. In addition, it is possible to use different combinations of various polyelectrolytes, each typically having different pKa constants and thus electrical conductivities. For example, polystyrene sulfonate (PSS) is recognized have a relatively high electrical conductivity. Various combinations of polyelectrolytes are thus contemplated for altering the electrical conductivity of different jetting liquid streams. In certain embodiments, such polyelectrolyte combinations employ poly(acrylic acid) (PAA), poly (acrylamide acrylic acid) (PAAm), poly(acrylamide acrylic acid) (PAAm), and/or poly(acrylamide-co-acrylic acid) (PAAm-co-AA).

In one aspect of the present disclosure, two distinct polyelectrolytes and a pH modifying agent are used in the jetting liquid that forms a core phase of the particles. One of the polyelectrolytes is a crosslinking agent or crosslinker, optionally present at a relatively low ratio to give specialized swelling properties to this phase, as described below. In certain aspects, a different ratio of the same polyelectrolytes can be used in the jetting liquid that forms the shell phase in the particles, where the crosslinking reaction can be carried out in this phase to make the particles stable with a specific swelling property.

Using a side-by-side arrangement of inlet flows to introduce multiple polymer solutions (jetting liquids) into an electric field, bi- and triphasic particles. In certain embodiments, co-jetting of aqueous solutions containing poly(acrylamide-co-acrylic acid) (PAAm-co-AA) in a first stream and poly (acrylic acid) (PAA) in a second stream to form multiphasic particles. Moreover, in various aspects, these particles can be stabilized via subsequent thermal or radiation induced crosslinking. Moreover, such multiphasic micro-components can be selectively surface-modified for each exposed phase surface (i.e., compartment). Biphasic nanoparticles formed in this manner have satisfying biocompatibility in short-term cytotoxicity studies.

In certain embodiments, the liquid streams used for electrified jetting comprise at least one polyelectrolyte and optionally additional polymers, which are typically provided in solution or suspension. Suitable solvents include by way of non-limiting example, water, $C_1$-$C_4$ alcohols, fluorinated alcohols (e.g., hexafluoroisopropanol), chloroform, methylene chloride, ethyl acetate, acetone, acetonitrile, n,n-dimethylformamide (DMF), triethylamine (TEA), and combinations thereof (e.g., 95:5 chloroform:dimethylforamide). As will be described in greater detail below, controlling the concentration of polymer in the liquid stream(s) being jetted, as well as the molecular weight of the polymer in the liquid stream, creates nano-components having a select pre-designated shape.

In various aspects of the present disclosure, the one or more polymers may be present in a liquid stream prior to electrified jetting or spraying at about 0.1 to about 100% by weight (on a wet basis). While the relative concentrations of polymers in a phase can vary greatly depending on the polymer, application, and process parameters used for forming the multiphasic micro-components, in certain aspects, a total amount of polymers (including all polyelectrolytes) is optionally present in a phase at about 0.5% to about 50% by weight; optionally from about 1% to 15% by weight of the liquid stream on a wet basis. In certain aspects, a total amount of polymers (including all polyelectrolytes) in each respective liquid stream is less than or equal to about 20 weight % of the total liquid stream on a wet basis; optionally at about 0.1 weight % to about 20 weight % of the total liquid stream weight; optionally at about 0.5 weight % to about 18 weight % of the total liquid stream weight; optionally at about 1 weight % to about 15 weight % of the total liquid stream weight; optionally at about 1 weight % to about 6 weight %; optionally at about 1 weight % to about 5 weight %; and in certain aspects, optionally at about 1 weight % to about 4 weight % of the liquid stream on a wet basis, depending on the desired morphology and particle size of the nano-components. As discussed above, concentration of the polymer in the liquid stream is one factor that controls the shape and size of the nano-component to be formed.

In certain aspects, the process dependent variables which are used to control particle shape to arrive at a predetermined multiphasic micro-component shape, include, but are not limited to, concentration of polymers in and conductivity of the respective jetting solutions, as well as flow rates of the jetting streams. The concentration of a polymer (along with other components) in a solution/jetting stream influences the viscosity, as does the molecular weight of the polymer (and other components, where present). Solvents or vehicles used in the jetting solution impact the dielectric constant of a respective jetting stream, viscosity, and vapor pressure. The flow rate of the jetting liquid stream relates to vapor pressure and stability of the jet formed. In certain aspects, the distance between a collector and a needle tip impacts the strength of the electric field applied, which in turn can impact the stability of the cone, as well as the cone shape itself and thus voltage, formed during jetting. Generally, so long as a stable cone jet is formed via correct distance between the electrode and the nozzle/needle tip, this variable does not have a significant impact on nano-component particle shape. Temperature, pressure, and humidity likewise impact the behavior of the jetting fluids and shapes formed, impacting solvent volatilization and applied voltage, for example.

While general trends may vary with different jetting compositions, by way of example, the morphology (aside from phase orientation) of the multiphasic micro-components can selected based on flow rate and concentration of polymers in the jetting liquid. For example, relatively low concentrations of polymer in a solvent/vehicle (for example, about 0.5 to about 2% w/w) used during electrified jetting produces discs. Relatively high concentrations (for example, about 4% w/w and greater) at the same flow rate (for example, 2 mL/hr) tends to produce spherical particles. Since the cone solidifies at lower flow rates when using a higher polymer concentration in solution, a relatively higher flow rate is typically desired, for example greater than or equal to about 2 mL/hour to form spheres. At slightly higher flow rates, the cone is more stable; however, the particle size of the spheres increases. Thus, in the regime where polymer concentration is greater and flow rates remain relatively low, spheres are formed. Where polymer concentration is lower and flow rates remain relatively low, discs are formed. When a polymer concentration is intermediate (for example, between a concentration that forms discs and a comparative concentration that forms spheres) and a higher flow rate is selected, rods may be formed. In this manner, the methods of the present invention provide the ability to create predetermined substantially round-shaped micro-components.

Inclusion of surface active agents in the liquid jetting compositions during electrified co-jetting creates micro-components having a greater softness in their morphology or shape. Thus, in certain embodiments, the liquid stream for jetting comprises at least one surfactant, such an anionic, nonionic, or zwitterionic surfactant. Particularly suitable anionic surfactants include, by way of non-limiting example, water-soluble salts of $C_8$-$C_{20}$ alkyl sulfates (e.g., sodium dodecyl sulfate (SDS) or sodium lauryl sulfate (SLS)), sulfonated monoglycerides of $C_8$-$C_{20}$ fatty acids, sarcosinates, taurates and the like. For example, an anionic surfactant like sodium dodecyl sulfate (SDS), or any other suitable surfactants known in the art, creates micro-components having a greater softness to their shapes. One or more surfactants are optionally present in a liquid jetting stream composition in a total amount of about 0.01% to about 10%, for example about 0.05% to about 5% or about 0.1% to about 2% by weight of the composition.

A multiphasic micro-component phase can be designed to have such properties by providing such materials within the material forming the phase, or may be provided by subsequent treating, reacting, or coating of the exposed phase surface after formation of the micro-component to achieve such properties. In certain embodiments, each phase can comprise a different active ingredient throughout the phase and may comprise a surface moiety (e.g., each phase's surface can be tagged with a different targeting moiety or active agent) or each phase can optionally have different surface properties. Specifically, at least one phase can be selected to be hydrophilic, hydrophobic, positively charged (cationic), negatively charged (anionic), surface active agent modified (e.g., PEG-ylated or covered with a zwitterion), superhydrophobic, superhydrophilic, olephobic, olephilic, and/or nanostructured, as described above.

In accordance with the present teachings, multiphasic micro-components can include two phases having the same property, such as both phases being hydrophilic. A multiphasic micro-component can be designed to have such properties by providing such materials within the material forming the phase, or may be provided by subsequent treating, reacting, or coating of the exposed phase surface after formation of the multiphasic microfiber to achieve such properties. Polymers within a selected phase can further be modified to interact and/or react with certain target moieties. For example, reactive groups on a polymer in a first phase may be cationic and the desired moiety for the surface is anionic and will be attracted to the surface of the first phase.

Polymers within a selected phase can further be modified to interact and/or react with certain target moieties. For example, reactive groups on a polymer in a first phase may be cationic and the desired moiety for the surface is anionic and will be attracted to the surface of the first phase. In other embodiments, the functional groups on the polymer may participate in a reaction with a functional group present on a moiety, such that they react and are bonded to the surface of the phase. For example, if a first phase of the multiphasic micro-component has a polymer with a —CHO functional group at the surface and the moiety to be attached to the first phase has a —$CH_2NH_2$ functional group, such groups have an affinity to form a —C=N covalent bond, thus, the surface of the first phase has an affixed moiety presented at the surface.

Moreover, in certain embodiments, each phase can comprise a different moiety (e.g., each phase can be tagged with a different targeting moiety or active agent) or can optionally have different surface properties. Specifically, at least one phase can be selected to be hydrophilic, hydrophobic, positively charged (cationic), negatively charged (anionic), surface active agent modified (e.g., PEG-ylated or covered with a zwitterion), superhydrophobic, superhydrophilic, olephobic, olephilic, and/or nanostructured, as described above.

In various aspects, one or more exposed phase surfaces comprise a moiety, such as those described in U.S. patent application Ser. No. 11/763,842. In certain aspects, the moiety may be provided to interact with the surrounding environment (for example, to avoid multiphasic micro-component detection by an immune system, provide optical properties to the multiphasic micro-component, provide binding to a biological or non-biological target, such as a medical device). In some aspects, the moiety is a binding moiety that provides the ability for the multiphasic micro-component to bind with a target. In certain aspects, the target may be an immune system cell, protein, enzyme, or other circulating agent associated with the animal).

In various aspects, one or more exposed phase surfaces comprise a moiety. In certain aspects, the moiety may be provided to interact with the surrounding environment (for example, to avoid multiphasic micro-component detection by an immune system, provide optical properties to the multiphasic micro-component, provide binding to a biological or non-biological target, such as a medical device). In some aspects, the moiety is a binding moiety that provides the ability for the multiphasic micro-component to bind with a target. In certain aspects, the target may be an immune system cell, protein, enzyme, or other circulating agent associated with the animal). The following is an exemplary list of non-limiting examples of suitable binding moieties for use with the multiphasic micro-component of the disclosure. Proteins, such as heat shock protein HSP70 for dentritic cells and folic acid to target cancer cells. Polysaccharides or sugars, such as silyilic acid for targeting leucocytes, targeting toxins such as saporin, antibodies, including CD 2, CD 3, CD 28, T-cells, and other suitable antibodies are listed in a Table at http://www.researchd.com/rdicdabs/cdindex.htm (Jun. 14, 2007), incorporated by reference. Binding moieties include aptamers, which are small oligonucleotides that specifically bind to certain target molecules, for example, Aptamer 0-7 which binds to osteoblasts; Aptamer A-10 which binds to prostate cancer cells; and Aptamer TTA1, which binds to breast cancer cells. Other exemplary binding moieties include peptides, such as CGLIIQKNEC (CLT1) and CNAGESSKNC (CLT 2) for binding to clots. Various peptides are well known in the art for binding to cells in the brain, kidneys, lungs, skin, pancreas, intestine, uterus, adrenal gland, and prostate, including those described in Pasqualini et al, "Searching for a molecular address in the brain," Mol Psychiatry. 1(6) (1996) pp. 421-2 and Rajotte, et al., "Molecular heterogeneity of the vascular endothelium revealed by in vivo phage display," J Clin Invest. 102(2) (1998) pp. 430-7, for example. Other binding biological binding moieties known or to be developed in the art are contemplated by the present disclosure.

Other conventional materials can be used to form the materials of respective phases, including solvents, plasticizers, fillers, bulking, or viscosity modifying agents, antioxidants, impurities, UV stabilizers, and where appropriate, flavoring, or fragrance substances.

In another aspect, a micro-component formed in accordance with the present teachings may have at least one phase that is dynamic or changes its physical or chemical properties in response to a change in the physical, chemical, or biological environment. Controlled variation of process parameters results in multiphasic polymeric micro-components having a substantially round shape, with either anisotropic multiphasic (e.g., Janus-type) or core-shell phase alignment geometries for the same polymer system. In certain embodiments, such electrohydrodynamic co-jetting is of two aqueous polymer solutions containing distinct polyelectrolytes, such as poly(acrylic acid) and poly(acrylamide-co-acrylic acid), respectively. In certain aspects, the present disclosure provides methods for preparation of core-shell particles with well-defined structures using electrohydrodynamic co-jetting. For those micro-components having a core-shell morphology, after cross-linking the particles are stable in aqueous or water-containing solutions and exhibit reproducible swelling behavior, while maintaining the original core-shell geometry (e.g., a reversible swelling behavior).

In certain aspects, the materials selected for use within the micro-components of the present disclosure can be designed to exhibit a swelling behavior in the presence of water or external stimuli, such as select pH ranges. The swelling behavior can be more pronounced in a core phase of the particle than in the shell phase, thus lending a desirable swelling property to the particles. For example, the swellable multiphasic micro-components can be used as suitable active agent carriers for delivery to a target (such as a drug carrier, for example) with the additional ability to control the release time of an active ingredient.

Additionally, in certain aspects, the multiphasic micro-components formed in accordance with the present teachings are selected to optionally undergo a reproducible and reversible physical transformation, such as swelling behavior, in response to an external stimulus present in the surrounding environment, while retaining and substantially returning to the original phase orientation after the stimuli is removed, reduced, or modified. In certain aspects, the change or response observed in the phase may be fully or at least partially reversible, once the stimulus is taken away. Exemplary stimuli to which micro-components can be designed to respond include light, change in pH, temperature, pressure, humidity, light, magnetic fields, electrical fields, other applied energy fields, or various chemicals stemming from either the human body or the environment, as described below. Thus, in certain aspects, one or more phases may comprise polymers or other components that respond upon exposure to an external stimulus, such as polymers or additives that respond to pH, temperature, pressure, humidity; dyes or other additives that change emission properties upon exposure to external UV radiation or light; particles or additives that are magnetic or conductive which respond to external energy fields, such as magnetic fields, electrical fields; and the like.

Many cross-linked polymeric materials are reversibly swellable, and thus have elastic and/or resilient properties (also referred to as "polymer memory recall") which are capable of elastic deformation, where such materials reversibly expand to a larger volume by interaction with an external stimulus and then return to an original contracted state post-deformation. In other words, in certain aspects, where a multiphasic micro-component comprises one or more phases that are substantially reversibly swellable, the phase material(s) spring back or recover (e.g., contract) to an original state after removing the external stimulus. By "substantially" it is meant that the phase material (e.g., polymeric material) exhibits the stated property or undergoes the stated action to the extent that the desired effect or result is achieved. For example, where a phase is "substantially reversibly swellable," the material undergoes substantially reversible deformation in the presence of an external stimulus, and after deformation from exposure to the stimulus, returns to the same or nearly the same initial volume, morphology and/or phase orientation. Thus, one or more of the phases of the micro-component material has an initial physical state, for example, an initial volume prior to exposure to the stimuli. The phase volume expands or swells in the presence of a stimulus. In embodiments where the swelling is reversible, the phase volume returns to nearly its initial physical state.

For instance, multiphasic micro-components are created in certain aspects to have at least one phase that swells when the micro-component is exposed to increased levels of moisture and/or humidity. As such, the color or other physical or chemical properties of the micro-components change or induce release of one or more active ingredients, such as an active agent, a drug, an enzyme, a fragrance, or a chemical of the micro-component. Other stimuli to which micro-components can be designed to respond include light, change in pH, temperature, magnetic fields, electrical fields, or various chemicals stemming from either the human body or the surrounding environment. In certain aspects, micro-component particles formed in accordance with the present teachings demonstrate pH-responsiveness when experiencing repeated switching of the environmental pH, for example between acidic (i.e., a pH of less than 7) and alkaline conditions (e.g., a pH of greater than 7).

For example, environmental responsiveness of the substantially round-shaped micro-components can be a key feature when designing capsules or particles for delivering an active agent to a target region. Environmental responsiveness can be a key aspect to novel drug delivery vehicles or for particles that can be used for clean-up and remediation of environmental contaminants or toxic waste. Thus, the present teachings provide methods for easy and relatively inexpensive production of environmentally responsive micro-components, such as core-shell micro-components for a variety of potential applications, including for delivery systems in micro-scales.

Accordingly, in certain aspects, electrohydrodynamic co-jetting forms anisotropic (e.g., Janus-type) particles, where respective phases have exposed surfaces (FIG. 3A), but can also be used for preparation of core-shell particles (FIG. 3D). Using side-by-side flow of miscible polymer solutions, electrohydrodynamic co-jetting presents an elegant and scalable route towards preparation of core-shell particles with otherwise difficult to prepare particle architectures, including particles with hydrophilic phases for both the shell and core regions.

In certain embodiments, electrohydrodynamic co-jetting of aqueous solutions of a mixture of PAAm-co-AA and PAA is used to form a range of different types of particles with distinct phases (e.g., compartments). By controlling relative conductivity of the two or more jetting solutions used in electrohydrodynamic co-jetting a transition occurs from anisotropic multiphasic (e.g., Janus) micro-components to core-shell micro-components, thus enabling selection of a predetermined phase alignment for the micro-component in accordance with the present teachings.

The degree to which a concentric geometry is achieved depends on the relative conductivities of the two jetting liquids that form solid phases (FIGS. 2B and 2C). The core-shell particles in FIGS. 2B and 2C have an average size distribution of about 1.9±0.4 µm (where scale bars shown for each figures is 8 µm). For example, with this material system, as the differences in conductivity change from a 6-fold (600%) to a 3-fold (300%) to a 1.3-fold (130%) difference, the resulting particles lose their core-shell character and begin to resemble anisotropic multiphasic (e.g., Janus) particles, where each phase has an exposed surface area. While core-shell particles have previously been fabricated using a coaxial needle geometry with one needle embedded in the second one, the present technology provides electrohydrodynamic co-jetting using a side-by-side arrangement of needles to form both anisotropic multiphasic (e.g., Janus) and core-shell particles. Moreover, the transition between the two characteristic morphologies is controlled by simply altering the relative conductivities of the jetting solutions.

Thus, in various aspects, the present disclosure provides methods of making a solid micro-component comprising a first phase and a second distinct phase, where the first electrical conductivity and the second electrical conductivity are selected to create a predetermined phase orientation in the solid particle. In certain aspects, where the polyelectrolyte polymers in both phases are PAA and PAAm-co-AA for electrohydrodynamic co-jetting experiments, a pH modifying agent, such as NaOH, can be used to alter the conductivity of the jetting solution, and the resultant particle architectures range from anisotropic (e.g., Janus) particles to core-shell particles (as shown in FIGS. 3A-3D). A ratio of the first electrical conductivity to the second electrical conductivity is about 1:1 to about 3:1 to from a predetermined phase orientation that is anisotropic in the multiphasic micro-component. Thus, in a PAA and PAAm-co-AA system, exemplary electrical conductivity ratios of the respective streams can range from about 5 mS/cm:5 mS/cm to about 15 mS/cm: 5 mS/cm, expressed in another way, a ratio of conductivities of about 1:1 to about 3:1. An anisotropic phase orientation is such that the first phase has a first exposed surface and the second phase has a second exposed surface.

Stated in another way, a conductivity mismatch ($\Delta\sigma$) between respective streams can be quantified by comparing relative conductivity of a first stream to conductivity of a second stream and may be less than or equal to about 300%, optionally less than or equal to about 200%, optionally less than or equal to about 100%, and optionally less than or equal to about 50%, optionally less than or equal to about 25%, optionally with no difference between respective conductivities for respective liquid jetting streams when the predetermined phase orientation is an anisotropic morphology (e.g., Janus), particularly for liquid jetting systems comprising water. In other aspects, a ratio of a first electrical conductivity of a first stream to conductivity of a second electrical conductivity of a second stream is selected to be at least about 6:1 and thus, the predetermined phase orientation is a core-shell morphology. In an exemplary PAA and PAAm-co-AA system, a pH modifying agent is added to the first stream such that exemplary electrical conductivity ratios of the respective streams are greater than or equal to about 30 mS/cm:5 mS/cm; optionally greater than or equal to about 32 mS/cm: 5 mS/cm.

Stated in another way, a conductivity mismatch ($\Delta\sigma$) between a first relative conductivity of a first stream to a second conductivity of a second stream is optionally greater than or equal to about 500%, optionally greater than or equal to about 600%, optionally greater than or equal to about 700%, optionally greater than or equal to about 800%, optionally greater than or equal to about 900%, and in certain aspects, may be greater than or equal to about 1000% for such polyelectrolyte jetting systems comprising water, when the predetermined phase orientation is core-shell morphology. Such relatively small compositional differences have a profound impact on the jetting behavior and the resulting phase orientation geometries.

In embodiments where the liquid stream includes carriers or solvents other than water, even smaller conductivity mismatches are required to form a predetermined phase orientation of core-shell particles. In such embodiments, a conductivity mismatch ($\Delta\sigma$) of a first conductivity of a first stream to a second conductivity of a second stream is optionally greater than or equal to about 200%, optionally greater than or equal to about 300%, optionally greater than or equal to about 400%, optionally greater than or equal to about 500%, optionally greater than or equal to about 600%, and the like. In such embodiments (where the liquid stream includes carriers or solvents other than water), a conductivity mismatch of a first relative conductivity of a first stream to a second conductivity of a second stream is optionally less than or equal to about 150%, optionally less than or equal to about 100%, less than or equal to about 50%, optionally less than or equal to about 20%, and optionally less than or equal to about 5%, optionally with no difference between respective conductivities for such polyelectrolyte systems, when the predetermined phase orientation is an anisotropic morphology for the micro-component (e.g., Janus particle).

In certain aspects, at least one phase of the multiphasic micro-component comprises at least one active agent or active ingredient. As appreciated by one of skill in the art, the first phase and the second phase (or additional distinct phases) can optionally include active ingredients that are the same or different from one another. Thus, in certain aspects, the multiphasic component comprises a first phase having at least one active ingredient and a second distinct phase having at least one distinct active ingredient. For example, where a multiphasic micro-component comprises a first phase and a second distinct phase, the first phase comprises one or more first active ingredients and the second phase optionally likewise comprises one or more second active ingredients. When present, one or more of the first active ingredients of the first phase can be distinct from the one or more second active ingredients of the second phase. Thus, the first phase may comprise at least one distinct active ingredient from the second phase.

Multiple phases of the composition may each respectively comprise at least one active ingredient and in some cases a plurality of distinct active ingredients. In other aspects, one or more of the distinct phases of the multiphasic nano-component may have a common active ingredient. The first and second phases (or additional phases) may contain one or more of the same active ingredients or different active ingredient cocktails (i.e., plurality or mixture of active ingredients). Moreover, core-shell particles show 450% increase in selective uptake of certain polar or conductive compounds, for example, selective uptake of 6-carboxyfluorescein over rhodamine B base dyes; in fact, this appears to be a general trend, as similar selectivities are observed for a number of different dyes. As such, selective uptake of certain compounds can be used both to introduce active ingredients to certain phases of the micro-component after formation or may be used to selectively absorb compounds from a surrounding environment in various applications, such as environmental remediation or diagnostics.

In various embodiments, at least one phase of the multiphasic micro-component comprises an active agent or ingredient. In various aspects, an active ingredient may be a material to be delivered to a target region for an intended affect or benefit. In certain aspects, the inventive multiphasic micro-components comprise multiple pharmaceutically active ingredients, such as exclusive or generic drugs, or combinations thereof. The active ingredient may vary depending on the application, for example, active ingredients contemplated herein include those for fragrances, perfumes, cosmetics, nutrients, supplements, nutraceutical, and food products, cleansers, home care products, laundry products, institutional and industrial applications (I&I), oral care, personal care, pharmaceutical products, diagnostic and imaging applications, pesticides, growth promoting agents, toxic and other waste storage, management, and treatment systems, environmental remediation products, and the like.

Thus, in certain variations, the multiphasic micro-components comprise one or more active ingredients selected from the group consisting of: a therapeutic active ingredient, a systemic active ingredient, a chemotherapy active ingredient, a localized active ingredient, an oral care active ingredient, a nutritional active ingredient, a personal care active ingredient, a cosmetic active ingredient, a diagnostic imaging indicator agent, pesticides, growth promoting agents, a home care active ingredient, an industrial or institutional active ingredient, and combinations thereof.

Thus, in various aspects, the multiphasic micro-components may be used in a wide variety of different types of compositions having an active ingredient and are not limited to the variations described herein. In certain aspects, the active ingredient is a pharmaceutical or cosmetic active compound or composition that diagnoses, prevents, or treats a physiological or psychological disorder or condition, provide prophylactic benefits, or can provide a cosmetic, sensory, or aesthetic benefit to an animal, such as a mammal. In certain aspects, an active ingredient prevents or treats a disease, disorder, or condition of hard or soft tissue in an organism, such as a mammal. In certain aspects, an active ingredient agent is targeted at organs, tissues, medical implants or devices, hair, skin, mouth, eyes, circulatory system, and the like. For example, in certain embodiments, the multiphasic micro-components having one or more active ingredients can be used in various pharmaceutical and/or cosmetic compositions.

A "pharmaceutically and/or cosmetically acceptable composition" refers to a material or combination of materials that are used with mammals or other organisms having acceptable toxicological properties for beneficial use with such an animal. Pharmaceutically and/or cosmetically acceptable compositions generally include drug and therapeutic compositions, oral care compositions, nutritional compositions, personal care compositions, cosmetic compositions, diagnostic compositions, and the like. Thus, in certain embodiments, the multiphasic micro-components may be used in a wide variety of different types of compositions having a bio-functional or bio-active material for safe use with animals, such as humans.

The ensuing description of suitable active ingredients is merely exemplary and should not be considered as limiting as to the scope of active ingredients which can be introduced into the multiphasic micro-components according to the present disclosure, as all suitable active ingredients known to those of skill in the art for these various types of compositions are contemplated. Certain suitable active ingredients, or pharmaceutically active ingredients or drugs, are known to those of skill in the art and include, but are not limited to, low-molecular weight molecules, quantum dots, natural and artificial macromolecules, such as proteins, sugars, peptides, DNA, RNA, and the like, polymers, dyes and colorants, inorganic ingredients including nanoparticles, nanomaterials, and nanocrystals, fragrances, and mixtures thereof, as will be discussed in more detail below.

Thus, pharmaceutical and/or cosmetic active ingredients may be used to repair or regenerate cells of an organ or tissue; treat or prevent a disease, such as an infectious disease (a bacterial, viral, or fungal infection) or a degenerative disease (Alzheimer's, amyotrophic lateral sclerosis (ALS)). For example, pharmaceutical and/or cosmetic active ingredients active ingredients may treat an auto-immune disorder (e.g., rheumatoid arthritis, systemic lupus erythematosus (SLE), inflammatory bowel disease (IBD)), allergies, asthma, osteoarthritis, osteoporosis, cancer, diabetes, arteriosclerosis and cardiovascular disease, stroke, seizures, psychological disorders, pain, acne, caries, gingivitis, periodontitis, an H2-agonist, human immunodeficiency, infections, and the like.

The description of suitable pharmaceutical and/or cosmetic active ingredients is merely exemplary and should not be considered as limiting as to the scope of active ingredients which can be introduced into the multiphasic micro-components according to the present disclosure, as all suitable bio-functional active agents and/or pharmaceutical and/or cosmetic active ingredients known to those of skill in the art for these various types of compositions are contemplated. Furthermore, a pharmaceutical and/or cosmetic active ingredient may have various functionalities and thus, can be listed in an exemplary class below; however, may be categorized in several different classes of active ingredients.

Suitable active ingredients for use in such pharmaceutically and/or cosmetically acceptable compositions are well known to those of skill in the art and include, by way of non-limiting example, those disclosed in the Merck Index, An Encyclopedia of Chemicals, Drugs, and Biologicals, Thirteenth Edition (2001) by Merck Research Laboratories and the International Cosmetic Ingredient Dictionary and Handbook, Tenth Ed., 2004 by Cosmetic Toiletry and Fragrance Association, and U.S. Pat. Nos. 6,589,562, 6,825,161, 6,063, 365, and 6,491,902, all to Shefer et al, each incorporated herein by reference. Each additional reference cited or described herein is hereby expressly incorporated by reference in its respective entirety.

More specifically, suitable pharmaceutical and/or cosmetic active agents include by way of non-limiting example, growth factors; growth factor receptors; transcriptional activators; translational promoters; anti-proliferative agents; growth hormones; anti-rejection drugs; anti-thrombotic agents; anti-coagulants; stem cell or gene therapies; antioxidants; free radical scavengers; nutrients; co-enzymes; ligands; cell adhesion peptides; peptides; proteins; nucleic acids; DNA; RNA; sugars; saccharides; nutrients; hormones; antibodies; immunomodulating agents; growth factor inhibitors; growth factor receptor antagonists; transcriptional repressors; translational repressors; replication inhibitors; inhibitory antibodies; cytotoxin; hormonal agonists; hormonal antagonists; inhibitors of hormone biosynthesis and processing; antigestagens; antiandrogens; anti-inflammatory agents; non-steroidal anti-inflammatory agents (NSAIDs); analgesics; COX-I and II inhibitors; antimicrobial agents; antiviral agents; antifungal agents; antibiotics; anti-proliferative agents; antineoplastic/antiproliferative/anti-miotic agents; anesthetic, analgesic or pain-killing agents; antipyretic agents, prostaglandin inhibitors; platelet inhibitors; DNA de-methylating agents; cholesterol-lowering agents; vasodilating agents; endogenous vasoactive interference agents; angiogenic substances; cardiac failure active ingredients; polysaccharides; sugars; targeting toxin agents; aptamers; quantum dots; nano-materials; nano-crystals; and combinations thereof.

In various aspects, one or more exposed phase surfaces of the micro-components comprise a biofunctional agent or moiety. In certain aspects, the presence of distinct exposed phases enables selective surface patterning with biofunctional agents, such as ligands, peptides (particularly cell adhesion peptides), cell adhesion molecules, proteins, nucleic acids, growth factors, hormones, antibodies, sugars, saccharides, nutrients, and the like. In certain aspects, the moiety may be provided to interact with the surrounding environment (for example, to avoid detection by an immune system, provide optical properties to the multiphasic microfiber, provide binding to a biological or non-biological target, such as cells or tissue or a medical device). In some aspects, the moiety is a binding moiety that provides the ability for the multiphasic micro-component to bind with a target. In certain aspects, the target may be a cell of an organism, such as germline or somatic cells, protein, enzyme, immune system cells, or other circulating cells or substances associated with the animal. The following discussion provides non-limiting examples of suitable binding moieties for use with the multiphasic micro-component components of the disclosure. Thus, suitable pharmaceutical and/or cosmetic active agents, which may optionally be surface bound moieties on one or more phases of the multiphasic micro-components.

Furthermore, the multiphasic micro-components optionally comprise pharmaceutical and/or cosmetic active agents that inhibit growth or response of certain targeted tissues, for example, cancer or immune system cells. In certain aspects, the multiphasic micro-components have one phase comprising a pharmaceutical and/or cosmetic active ingredients agent to promote growth, proliferation, differentiation and/or repair of certain target cells, while another distinct pharmaceutical and/or cosmetic active ingredients agent may inhibit growth of distinct target cells. For example, a multiphasic micro-components optionally includes growth factors, growth factor receptors, transcriptional activators, and translational promoters for promoting cell growth and may further optionally include cell growth inhibitors such as antiproliferative agents, growth factor inhibitors, growth factor receptor antagonists, transcriptional repressors, translational repressors, replication inhibitors, inhibitory antibodies, antibodies directed against growth factors, biofunctional molecules consisting of a growth factor and a cytotoxin, biofunctional molecules consisting of an antibody and a cytotoxin, and the like.

Macromolecules include a wide range of compounds, generally including polymers and biomolecules having relatively large molecular weights. Such macromolecules can be naturally occurring or synthesized, some of which have been described above. Amino acids, peptides (amino acids linked via peptide bonds); polypeptides (linear chains of peptides); and proteins (primary, secondary, and tertiary folded polypeptides) are all contemplated as active ingredients. In certain variations, examples of the pharmaceutical and/or cosmetic active ingredients agents include, but are not limited to, peptides and proteins, including erythropoietin (EPO), stem cell factor (SCF), vascular endothelial growth factor (VEGF), keratinocyte transforming growth factor (TGF), fibroblast growth factor (FGF), epidermal growth factor (EGF), cartilage growth factor (CGF), nerve growth factor (NGF), keratinocyte growth factor (KGF), skeletal growth factor (SGF), osteoblast-derived growth factor (BDGF), hepatocyte growth factor (HGF), insulin-like growth factor (IGF), cytokine growth factor (CGF), stem cell factor (SCF), platelet-derived growth factor (PDGF), endothelial cell growth supplement (ECGS), colony stimulating factor (CSF), growth differentiation factor (GDF), integrin modulating factor (IMF), calmodulin (CaM), thymidine kinase (TK), tumor necrosis factor (TNF), growth hormone (GH), cartilage transcription factor SRY-related HMG-box gene 9 (Sox-9), bone morphogenic proteins (BMP) (e.g., BMP-2, BMP-3, BMP-4, BMP-5, BMP-6 (Vgr-1), BMP-7 (PO-1), BMP-8, BMP-9, BMP-10, BMP-11, BMP-12, BMP-14, BMP-15, BMP-16, and the like), interferon, interleukins (e.g., IL-1, IL-2, IL-3, IL-4, IL-5, IL-6, IL-7, IL-8, IL-9, IL-10, IL-11, IL-12, IL-15, and the like), cytokines, integrins, selectins, cadherins, collagen, elastin, fibrillins, nectins (e.g., fibronectin, hemonectin), laminin, glycosaminoglycans, vitronectin, thrombospondin, heparan sulfate, dermantan, chondrotin sulfate (CS), hyaluronic acid (HA), proteoglycans, transferrin, cytotactin, tenascin, lymphokines, cell adhesion molecules, (e.g., neural cell adhesion molecules (N-CAMS), intercellular cell adhesion molecules (ICAMS), vascular cell adhesion molecules (VCAM), platelet-endothelial cell adhesion molecules (PECAM)).

Proteins, such as heat shock protein HSP70 for dendritic cells and folic acid to target cancer cells can be suitable ligand moieties for the surface of one or more phases of a micro-component. Other cell adhesion peptides, such as antibodies, sugars, nucleotides, DNA, RNA, and the like known in the tissue and bioengineering arts may also be suitable moieties or ligands for the surface(s) of respective phases of the multiphasic micro-components. Exemplary toxins for use as active ingredients include saporin and Botulinum toxins. Exemplary sugars include silyilic acid leucocytes and glucuronic acid, for example. Other suitable surface moieties include polysaccharides or sugars, such as silyilic acid for targeting leucocytes, targeting toxins such as saporin, antibodies, including CD 2, CD 3, CD 28, T-cells, and other suitable antibodies are listed in a Table at http://www.researchd.com/rdicdabs/cdindex.htm (Jun. 14, 2007), incorporated by reference.

Other suitable binding moieties include aptamers, which are small oligonucleotides that specifically bind to certain target molecules, for example, Aptamer O-7 which binds to osteoblasts; Aptamer A-10 which binds to prostate cancer cells; and Aptamer TTA1, which binds to breast cancer cells. Other binding biological binding moieties suitable for tissue engineering or cell cultures known or to be developed in the art are contemplated by the present disclosure. As noted above, such pharmaceutical and/or cosmetic active ingredients agents are optionally included throughout one or more phases of the multiphasic micro-components or may be provided only on the surface of an exposed phase (as a surface bound moiety).

Further, the multiphasic micro-components may include pharmaceutical active ingredients that are immunotherapeutic agents, such as antibodies and immunomodulators, which may inhibit growth of certain target cells, which include by way of non-limiting example, HERCEPTIN™ (trastuzumab, humanized IgG1 antibody for metastatic breast cancer); RITUXAN™ (Rituximab, chimeric IgG1 antibody for NHL); PANOREX™ (17-1A monoclonal antibody), BEC2 (anti-idiotypic antibody), IMC-C225 (monoclonal antibody); VITAXIN™ (monoclonal antibody); CAMPATHI/H™ (DNA-derived humanized monoclonal antibody), 5G1.1 (humanized IgG for treatment of rheumatoid arthritis (RA), systemic lupus erythematosus (SLE), nephritis); 5G1.1-SC (humanized ScFv antibody for cardiopulmonary bypass, infarction, angioplasty and other cardiac procedures); ABX-CBL (humanized antibody for graft-versus-host disease (GvHD)); ABX-CBL (murine CD147 antibody for allograft rejection); ABX-IL8 (humanized IL-8 antibody for psoriasis); AD-159 (humanized antibody for human immunodeficiency virus (HIV)); AD-439 (humanized antibody for HIV); ANTEGREN™ (humanized IgG antibody for multiple sclerosis); Anti-CD11a (humanized IgG1 antibody for psoriasis); Anti-CD18 (humanized Fab'2 antibody for myocardial infarction); Anti-LFA1 (murine Fab'2 antibody for allograft rejection); Anti-VEGF (humanized IgG1 antibody for cancer); ANTOVA™ (humanized IgG antibody allograft rejection); BEC2 (murine IgG antibody for lung cancer); BIRR-1 (murine IgG2a antibody for stroke); BTI-322 (Rat IgG antibody GvHD); C225 (chimeric IgG antibody for head and neck cancers); CAT-152 (humanized antibody glaucoma); CDP571 (humanized IgG4 antibody for Crohn's disease); CDP850 (humanized antibody for psoriasis); CORSEVIN M™ (chimeric antibody as an anticoagulant); D2E7 (humanized antibody for RA); Hu23F2G (humanized IgG antibody for stroke and MS); ICM3 (humanized antibody for Psoriasis); IDEC-114™ (primatized antibody for psoriasis); IDEC-131™ (humanized antibody for SLE, multiple sclerosis (MS)); IDEC-151™ (primatized IgG1 for RA); IDEC-152™ (primatized antibody for asthma and allergic reactions); INFLIXIMAB™ (chimeric IgG1 antibody for RA, Crohn's disease); LDP-01 (humanized IgG antibody for stroke, allograft rejection); LDP-02 (humanized antibody for ulcerative colitis); LDP-03/CAMPTATH 1H™ (humanized IgG1 antibody for chronic lymphocytic leukemia (CLL)); Lym-1 (chimeric antibody for non-Hodgkin's lymphoma (NHL)); LYMPOCIDE™ (humanized antibody for NHL); MAK-195F (murine Fab'2 antibody for toxic shock); MDX-33 (human antibody for autoimmune haematogical disorders); MDX-CD4 (human IgG antibody for RA); MEDI-500 (murine IgM antibody for treating GvHD); MEDI-507 (humanized antibody for psoriasis and GvHD); OKT4A (humanized IgG antibody for allograft rejection); ORTHOCLONE™ (humanized IgG antibody for autoimmune disease); ORTHOCLONE™/anti-CD3 (murine mIgG2a antibody for allograft rejection); OSTAVIR™ (human antibody for Hepatitis B); OVAREX™ (murine antibody for ovarian cancer); PANOREX 17-1A™ (murine IgG2a antibody for colorectal cancer); PRO542 (humanized antibody for HIV); PROTOVIR™ (humanized IgG1 antibody for cytomegalovirus infection (CMV)); REPPRO/ABCIXIMAB™ (chimeric Fab antibody for complications from coronary angioplasty); rhuMab-E25 (humanized IgG1 antibody for asthma and allergies); SB-240563 (humanized antibody for asthma and allergies); SB-240683 (humanized antibody for asthma and allergies; SCH55700 (humanized antibody for asthma and allergies); SIMULECT™ (chimeric IgG1 antibody for allograft rejection); SMART a-CD3™ (humanized IgG antibody for autoimmune disease, allograft rejection, and psoriasis); SMART M195™ (humanized IgG antibody for Acute Myeloid Leukemia (AML)); SMART I D10™ (antibody for NHL); SYNAGIS™ (humanized IgG1 antibody for RSV); VITAXIN™ (humanized antibody for Sarcoma); and ZENAPAX™ (humanized IgG1 antibody for allograft rejection), and combinations thereof.

In certain aspects, a multiphasic micro-component may comprise pharmaceutical active ingredient immunotherapeutic agent selected from the group consisting of: Smart M195™, LYMPHOCIDE™, Smart I D10™, ONCOLYM™, rituximab, gemtuzumab, trastuzumab, Anti-LFA1; ANTOVA™; ABX-CBL; ABX-CBL; BTI-322, CORSEVIN M™, IDEC-152; LDP-01; MAK-195F; MEDI-507; OKT4A ORTHOCLONE™/anti-CD3; REPPRO/ABCIXIMAB™; SIMULECT™; SMART a-CD3 ™; ZENAPAX™, and combinations thereof.

In certain other embodiments, the multiphasic micro-components may further comprise a hormonal treatment agent, such as hormonal agonists, hormonal antagonists (e.g., flutamide, tamoxifen, leuprolide acetate (LUPRON™), LH-RH antagonists), inhibitors of hormone biosynthesis and processing, steroids (e.g., dexamethasone, retinoids, betamethasone, cortisol, cortisone, prednisone, dehydrotestosterone, glucocorticoids, mineralocorticoids, estrogen, testosterone, progestins), antigestagens (e.g., mifepristone, onapristone), and antiandrogens (e.g., cyproterone acetate), by way of non-limiting example.

In certain variations, the multiphasic micro-components of the present disclosure optionally comprise one or more active ingredients selected from: anti-rejection drugs (such as cyclosporine), anti-inflammatory agents, non-steroidal anti-inflammatory agents (NSAIDs), analgesics, COX-I and II inhibitors, antioxidants, antimicrobial agents, including antiviral, antifungal, antibiotics and the like, and combinations and equivalents thereof. For example, useful anti-inflammatory agents include steroids, such as glucocorticoids, betamethasone, dexamethasone, prednisolone, corticosterone, budesonide, estrogen, sulfasalazine, and mesalamine, while indomethacin, ibuprofen, naproxen, and the like are suitable NSAIDs for incorporation into one or more phases of the multiphasic micro-components. Suitable antibiotic agents, include penicillin, cefoxitin, oxacillin, tobranycin, rapamycin, by way of non-limiting example.

Other pharmaceutically and/or cosmetically active agents also include non-genetic therapeutic agents, such as: anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid, amlodipine and doxazosin; antineoplastic/ antiproliferative/anti-miotic agents such as paclitaxel, 5-fluorouracil, cisplatin, vinblastine, cladribine, vincristine, epothilones, methotrexate, azathioprine, adriamycin and mutamycin; endostatin, angiostatin and thymidine kinase inhibitors, Taxol™ and its analogs or derivatives; anesthetic or pain-killing agents such as lidocaine, bupivacaine, and ropivacaine; anti-coagulants such as D-Phe-Pro-Arg chloromethyl ketone, RGD peptide-containing compound, heparin, anti-thrombin compounds, anti-thrombin antibodies, platelet receptor antagonists, anti-platelet receptor antibodies, aspirin (aspirin is also classified as an analgesic, antipyretic and anti-inflammatory drug), dipyridamole, protamine, hirudin, prostaglandin inhibitors, platelet inhibitors and tick anti-platelet peptides; DNA de-methylating drugs such as 5-azacytidine, (also categorized as a RNA or DNA metabolite that inhibits cell growth and induce apoptosis in certain cancer cells); cholesterol-lowering agents; vaso-dilating agents; and agents that interfere with endogenous vasoactive mechanisms; anti-oxidants, such as probucol; angiogenic substances, such as acidic and basic fibroblast growth factors, estrogen including estradiol (E2), estriol (E3) and 17-Beta Estradiol; drugs for heart failure, such as digoxin, beta-blockers, angiotensin-converting enzyme (ACE) inhibitors including captopril, enalopril, and statins and related compounds, and any combinations thereof.

In some aspects, it may be desirable to avoid detection of the multiphasic micro-components by the animal's immune system, for example, to prevent removal or an immune system rejection response from the body by macrophages and the like. The present disclosure contemplates various methods to prevent an animal's immune system from identifying the multiphasic micro-components and mounting an immune system response. In addition to the immunomodulator agents discussed above, another method to avoid immune response can be to provide moieties on the surface of at least one phase that is a "cloaking agent," which prevents the animal's immune system from recognizing a foreign body. Examples of such moieties include modified carbohydrates, such as sialic acid, dextran, pullulan, or glycolipids, hyaluronic acid, chitosan, polyethylene glycols, and combinations thereof. Other examples of immune system cloaking agents known in the art or to be discovered are further contemplated.

Yet other suitable pharmaceutically active ingredients or drugs, known to those of skill in the art, include but are not limited to, low-molecular weight molecules, quantum dots, natural and artificial macromolecules, such as proteins, sugars, peptides, DNA, RNA, and the like, natural polymers, dyes and colorants, inorganic ingredients including nanomaterials, and nano-crystals, fragrances, and mixtures thereof.

A variety of low molecular weight molecules can be included in one or more phases of the multiphasic micro-components, particularly those having a molecular weight of less than about 10,000, optionally less than about 1,000, and optionally less than about 500. Such molecules include pharmaceutical therapeutic drugs, which by way of non-limiting example, including chemotherapeutic drugs, for example, doxorubicin (molecular mass of about 543.5 g/mol); paclitaxel or Taxol™ (molecular mass of about 853.9 g/mol), cholesterol lowering drug, lovastatin (molecular mass of about 404.5 g/mol), NSAID analgesic ibuprofen (molecular mass of 206.3 g/mol). Quantum dots are optically active nano-structures, for example, cadmium tellurium (CdTe).

Useful nano-components and nano-crystals generally having a particle size of less than about 50 nm, optionally less than about 20 nm, and in some aspects, less than 10 nm. Useful non-limiting active ingredient nanoparticles include magnesium oxide, and metal based nano-particles, comprising gold, silver, and the like. Suitable active ingredient nanocrystals include magnetite ($Fe_3O_4$).

In other variations, additional ingredients that can be used in the multiphasic microfibers are not biofunctional, but rather are used for diagnostic purposes, such as in various diagnostic medical imaging procedures (for example, radiographic imaging (x-ray), fluorescence spectroscopy, Forster/fluorescent resonance energy-transfer (FRET), computed tomography (CT scan), magnetic resonance imaging (MRI), positron emission tomography (PET), other nuclear imaging, and the like). Diagnostic active ingredients for use with diagnostic imaging include contrast agents, such as barium sulfate for use with MRI, for example, or fluorescein isothiocyanate (FITC).

In other aspects, multiphasic micro-components having an active ingredient can be used in an oral care composition, which can be in the form of a dentifrice, such as toothpastes, toothpowders, and prophylaxis pastes, confectionaries, including gums, beads and chews, films, professional polishing formulations or any other form known to one of skill in the art.

Non-limiting examples of oral care active ingredients among those useful in multiphasic micro-components for use in an oral care composition include anti-plaque agents, anti-gingivitis agents, antimicrobial agents, anti-tartar agents, anti-caries agents, anti-viral agents, anti-inflammatory agents, antioxidants, whitening agents, desensitizing agents, vitamins, nutrients, natural extracts and essential oils, compatible enzymes, periodontal actives, breath freshening agents, malodor control agents, salivary stimulants, pH modifying agents, analgesics and combinations and mixtures thereof. Other oral active ingredients among those useful herein are also disclosed in U.S. Pat. Nos. 6,685,921 to Lawlor; 6,132,702 to Witt et al., and 5,741,138 to Rice et al.

In other aspects, multiphasic micro-components can be used in personal care compositions, such as soaps, bath gels, body washes, exfoliating scrubs, shampoos, lotions, serums, creams, sunscreens, self-tanning products, antiperspirant and deodorant products, nail care products, cosmetics, and the like. For personal care and cosmetic compositions, suitable active ingredients include anti-oxidants; free radical scavengers; moisturizers; depigmentation agents; skin lightening agents; reflectants; humectants; antimicrobial agents; antibacterial agents; allergy inhibitors; anti-acne agents; anti-aging agents; anti-wrinkling agents, antiseptics; analgesics; keratolytic agents; anti-inflammatory agents; fresheners; healing agents; anti infective agents; inflammation inhibitors; wound healing promoters; peptides, polypeptides; proteins; deodorants; antiperspirants; skin emollients; skin moisturizers; tanning agents; skin lightening agents; antifungals; depilating agents; counterirritants, non-steroidal soothing agents, anti-itch agents, poison ivy agents; poison oak agents; burn products; make-up preparations; vitamins; amino acids and their derivatives; herbal extracts; cooling agents; heating agents; skin conditioners; chelating agents; cell turnover enhancers; coloring agents; sunscreens; nourishing agents; moisture absorbers; sebum absorbers; skin penetration enhancers, pigments, dyes, fragrances, and the like, such as those disclosed in U.S. Pat. No. 6,825,161 to Shefer et al.

In alternate variations, the multiphasic micro-components s can be used in cleansers, institutional and industrial compositions, and/or home care compositions including powders, pastes, dishwashing liquids and automatic dishwasher detergents, fabric detergents and softeners, sanitizers, and hard surface cleansers, by way of non-limiting agents. Active ingredients include enzymes, bleaching agents, surface active agents, phosphates, builders, anti-deposition agents, and the like.

In certain aspects, the multiphasic micro-components can be used in exemplary nutritional compositions, such as food, drinks, pills, and supplements. Suitable active ingredients include those that are nutrients, such as vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophane, L-lysine, methionine, threonine, levocarnitine and L-carnitine), lipotropics (such as choline, inositol, betaine, and linoleic acid), fish oil (including components thereof such as omega-3 (N-3) polyunsaturated fatty acids, eicosapentaenoic acid and docosahexaenoic acid), coenzyme Q10, and mixtures thereof.

In various aspects, a multiphasic micro-component delivers an effective amount of the active ingredient to a target region. An "effective" amount of an active ingredient is an amount that has a detectable effect for its intended purpose and/or benefit. Preferably, the effective amount is sufficient to have the desired therapeutic, nutritional, cleansing, aesthetic, diagnostic, and/or prophylactic effect on the target region to which the composition comprising the multiphasic micro-components is administered. The specific effective amount of the active ingredient, including appropriate dosages and concentrations, will vary with such factors as the composition in which the active ingredient is provided, the site of intended delivery, the route of administration, the particular condition or subject being treated, the nature of concurrent therapy (if any), the specific active used, the specific dosage form, and the carrier employed, all of which are well known to those of skill in the art.

In yet other alternate embodiments, the active agent is a pesticide, such as an herbicide, insecticide or insect growth regulator; fungicide; or rodenticide. A list of exemplary pesticides includes acaricides, algicides, anti-feedants, avicides, bactericides, bird repellents, chemosterilants, fungicides, herbicide safeners, herbicides, insect attractants, insect repellents, insecticides, mammal repellents, mating disruptors, molluscicides, nematicides, plant activators, plant-growth regulators, rodenticides, synergists, and virucides, and combinations thereof.

By way of non-limiting example, suitable insecticides include 2,4-D, esters and salts; Atrazine; Bensulide; Bromacil; Chlorthal-dimethyl; Dicamba, salts and esters; Diquat dibromide; Diuron; Fluazifop-butyl; Glyphosate, salts and esters; Halosulfuron; Isoxaben; Nonanoic acid; Oryzalin; Oxadiazon; Pendimethalin; Tebuthiuron; Triclopyr, esters and salts; Trifluralin; and Ziram; suitable examples of insecticides or insect growth regulators include Acephate; Avermectin; *Bacillus thuringiensis*; Bifenthrin; Boric acid; Carbaryl; Chlorpyrifos; Cyfluthrin; Cypermethrin; Deltamethrin; Diazinon; Disodium octaborate tetrahydrate; Esfenvalerate; Fipronil; Hydramethylnon; Hydroprene; Imidacloprid; Linalool; Malathion; Methoprene; Muscalure; N-Octyl bicycloheptene dicarboximide; Phenothrin; Piperonyl butoxide; Potash soap; Propetamphos; Propoxur; Pyrethrins; Silica aerogel; and Trichlorfon; suitable examples of fungicides include Benomyl; Chlorothalonil; Maneb; PCNB; and sulfur; suitable example of rodenticides include Bromadiolone; Chlorophacinone; and Diphacinone.

A list of exemplary herbicides is as follows: amide herbicides including chloroacetanilide herbicides (such as alachlor and metolachlor); antibiotic herbicides; aromatic acid herbicides including benzoic acid herbicides (such as chloramben and dicamba), phthalic acid herbicides, picolinic acid herbicides, and quinolinecarboxylic acid herbicides; arsenical herbicides; benzoylcyclohexanedione herbicides; benzofuranyl alkylsulfonate herbicides; carbamate herbicides; carbanilate herbicides; cyclohexene oxime herbicides; cyclopropylisoxazole herbicides; dicarboximide herbicides; dinitroaniline herbicides (such as trifluralin and pendimethalin); dinitrophenol herbicides; diphenyl ether herbicides; dithiocarbamate herbicides; halogenated aliphatic herbicides; imidazolinone herbicides; inorganic herbicides; nitrile herbicides; organophosphorus herbicides; phenoxy herbicides (such as 2-4D (also called 2,4-dichlorophenoxy acetic acid) and Mecoprop); phenylenediamine herbicides; pyrazolyloxyacetophenone herbicides; pyrazolylphenyl herbicides; pyridazine herbicides; pyridazinone herbicides (such as Norflurazon™); pyridine herbicides; pyrimidinediamine herbicides; quaternary ammonium herbicides; thiocarbamate herbicides (including butylate and EPTC); thiocarbonate herbicides; thiourea herbicides; triazine herbicides (such as atrazine and simazine); triazinone herbicides (such as METRIBUZIN™); triazole herbicides; triazolone herbicides; triazolopyrimidine herbicides; uracil herbicides; urea herbicides; ROUNDUP™ (manufactured by Monsanto Co. of St. Louis, Mo.); CHLOROPROPHAM™; SURFLAN™ (manufactured by Southern Agricultural Insecticides, Inc. of Palmetto, Fla.); and CLOMAZONE™.

Exemplary microbial pesticides include *bacillus thuringiensis* and mycorrhizal fungi. Exemplary insecticides include thiodan, diazinon, and malathion. Exemplary fungicides include ALIETTE™ (aluminum tris (o-ethylphosphenate)); ROVRAL™ (iprodione); MANCOZEB™; SOVRAN™ (kresoxim-methyl); FLINT™ (trifloxystrobin); RIDOMIL™ (Mefenoxam); RIDOMIL GOLD™ methoxyacetylamino-2-R-2[2,6-dimethylphenyl-propionic acid methyl ester); DIVIDEND™ (difenoconazole); SOILGARD™ (*gliocladium virens*); BRAVO™ (chlorothalonil); VITAVAX™ (carboxin); THIRAM™ (tetramethylthiuram disulfide); MAXIM™ (fludioxonil); QUADRIS™ (azoxystrobin); and ELITE™ (tebuconazole).

Other suitable active agents include growth-promoting agents, such as include fertilizers, bioactive materials, plant-growth hormones and regulators, and soil-based nutrients.

Exemplary plant-growth regulators include antiauxins, such as, for example, 2,3,5-tri-iodobenzoic acid; auxins, such as, for example, 2,4-D; cytokinins, such as, for example, kinetin; defoliants, such as, for example, metoxuron; ethylene inhibitors; ethylene releasers, such as, for example, ACC and gloxime; gibberellins; growth inhibitors; growth retardants; growth stimulants; derivatives thereof; and mixtures thereof.

A list of exemplary soil-based nutrients includes calcium, magnesium, potassium, phosphorus, boron, zinc, manganese, copper, iron, sulfur, nitrogen, molybdenum, ammonium phosphate, fish meal, derivatives, and combinations thereof.

Thus, in summary, in certain aspects of the present disclosure, the multiphasic micro-components comprise one or more active ingredients selected from the group consisting of: low-molecular weight molecules, natural and artificial macromolecules, growth factors, growth factor receptors, transcriptional activators, translational promoters, anti-proliferative agents, growth hormones, anti-rejection drugs, anti-thrombotic agents, anti-coagulants, stem cell or gene therapy agents, antioxidants, free radical scavengers, nutrients, co-enzymes, ligands, peptides, proteins, nucleic acids, DNA, RNA, sugars, saccharides, nutrients, hormones, antibodies, immunomodulating agents, growth factor inhibitors, growth factor receptor antagonists, transcriptional repressors, translational repressors, replication inhibitors, inhibitory antibodies, cytotoxin, hormonal agonists, hormonal antagonists, inhibitors of hormone biosynthesis and processing, antigestagens, antiandrogens, anti-inflammatory agents, analgesics, non-steroidal anti-inflammatory agents (NSAIDs), COX-I and II inhibitors, antimicrobial agents, antiviral agents, antifungal agents, antibiotics, antineoplastic/antiproliferative/anti-miotic agents, anesthetic, analgesic or painkilling agents, antipyretic agents, prostaglandin inhibitors, platelet inhibitors, DNA de-methylating agents, cholesterol-lowering agents, vasodilating agents, endogenous vasoactive interference agents, angiogenic substances, cardiac failure active ingredients, polysaccharides, sugars, targeting toxin agents; aptamers, quantum dots, nano-materials, nano-crystals, localized drugs, tooth whitening agents, skin whitening agents, anti-caries agents, anti-tartar agents, anti-plaque agents, anti-adhesion agents, desensitizing agents, malodor control agents, flavoring agents, anti-aging agents, salivary stimulants, periodontal actives, depigmentation agents, skin lightening agents, reflectants, humectants, allergy inhibitors, anti-acne agents, anti-aging agents, anti-wrinkling agents, antiseptics, keratolytic agents, fresheners, healing agents, inflammation inhibitors, wound healing promoters, deodorants, antiperspirants, skin emollients, tanning agents, antifungals, depilating agents, counterirritants, non-steroidal soothing agents, anti-itch agents, poison ivy agents, poison oak agents, burn alleviation agents, vitamins, cooling agents, heating agents, chelating agents, anti-psoriasis agents, anti-dandruff agents, skin conditioners, moisturizing agents, emollients, humectants, occlusive agents, skin lipid fluidizers, deodorant active agents, antiperspirant active agents, skin and/or scalp sensates, skin and/or scalp soothing and/or healing agents, astringents, opacifying agents, biocides, natural and synthetic extracts and essential oils, nutrients, enzymes, proteins, amino acids, vitamins, analgesics, sunscreen agents, UV absorbers, antioxidants, antibiotics, exfoliants, cell turnover enhancers, coloring agents, sunscreens, nourishing agents, moisture absorbers, sebum absorbers, skin penetration enhancers, colorants, pigments, dyes, flavors, fragrances, detergents, fabric softeners, hard surface cleaning agents, bleaching agents, surface active agents, phosphates, builders, anti-deposition agents, pesticides, growth-promoting agents, imaging or contrast agents, and combinations thereof.

Experimentally, electrohydrodynamic co-jetting employs parallel extrusion of two miscible solvents through a macroscopic nozzle (e.g., 134 of FIG. 2A) with a diameter of 0.46 mm. A counter electrode 146, which acts as collection reservoir, is placed about 33 cm away from the tip of the nozzle 134. The polymer solution 134 is then accelerated towards the collection electrode 146 by application of an electrical potential 142 of about 16 kV, which corresponds to an electric field of about 48,500 V/m. Due to acceleration in the electric field, the polymer thread is rapidly elongated resulting in a reduction in diameter by several orders of magnitude. The reduction in thread diameter is accommodated by a dramatic increase in surface area, which, in turn, results in instantaneous evaporation of the solvent and solidification of polymers and other additives that are initially dissolved in the solvent. Because the solidification process is much faster than competing transport/mixing processes between individual solutions, the original droplet geometry is maintained during the co-jetting, resulting in solid particles with defined respective phases or compartments.

As summarized in Table 1 (below), base polymers PAA and PAAm-co-AA are used for all solutions used in the electrohydrodynamic co-jetting experiments. Addition of a pH modifying agent, such as NaOH, alters the conductivity of the jetting solution, and the resultant particle architectures range from anisotropic multiphasic (e.g., Janus) particles to core-shell particles. Characteristic examples are shown in FIGS. 3A-3D. In the case of the anisotropic Janus-type particles, i.e., (biphasic)$_{ab}$ particles (FIG. 3A), a ratio of PAA and PAAm-co-AA is the same in both phases. It is important to note that the conductivity of both jetting solutions [a'] and [b] are the same (5 mS/cm). In contrast, simply increasing the PAA ratio of one jetting solution results in transition from Janus-type particles to well-defined core-shell particles (core-shell)$_{ab}$ particles (FIG. 3D). In the case of (core-shell)$_{ab}$ particles, addition of NaOH to only one jetting solution resulted in a conductivity mismatch ($\Delta\sigma$), where the conductivity of solution [a] is about 6 times higher than that of solution [b]. Such relatively small compositional differences have a profound impact on the jetting behavior and the resulting particle geometries.

Experiment 1

Materials: PAAm-co-AA (MW=200,000 g mol-1, 10% carboxyl) is obtained from Polysciences, Inc., PAA (MW=250,000 g mol$^{-1}$, 35 wt % solution in water), FITC-dextran (MW=250,000 g mol-1) and TRITC-dextran (MW=155,000 g mol-1) are purchased from Sigma-Aldrich. All chemicals are used as received. De-ionized water is used for preparation of the solutions.

Polymer solutions used for co-jetting: Polymer solutions used for co-jetting are made of PAA (13.1% w/v)/PAAm-co-AA (0.044% w/v)/NaOH (2.19% w/v)/FITC-dextran (0.4% w/v) (solution [a]), PAAm-AA (5% w/v)/PAA (0.9% w/v)/TRITC-dextran (0.4% w/v) (solution [b]) and PAAm-AA (5% w/v)/PAA (0.9% w/v)/FITC-dextran (0.4% w/v) (solution [a']).

Electrified co-jetting with side-by-side dual capillaries: The solutions are separately charged into 1 ml syringes. A dual-channel tip (FibriJet, Micromedics, Minnesota, USA) apparatus, such as that shown in FIG. 2 has two capillaries (26 gauge, length of 4 inch) is connected to the syringes and is placed 33 cm above a surface of aluminum foil. In order to obtain stable polymer jetting, a flow rate of 100 µL/h and a voltage difference of 16-17 kV between the capillaries and the collecting surface are applied.

Crosslinking reaction: Crosslinking reaction between amine and carboxylic groups present in the respective phases of the particles is performed by incubating the particles at 170° C. for 2 hours.

Confocal microscopy: Confocal microscopy images are obtained using a SP$_2$ confocal laser scanning microscope (Leica, USA). FITC and TRITC are excited by Ar/ArKr (488 nm) or GreNe (543 nm) lasers, respectively. Fluorescence emissions are collected in the range of 508-523 nm for FITC and 568-583 nm for TRITC.

Scanning electron microscopy (SEM): Samples are used without further coating with a conductive layer for SEM imaging using FEI quanta 200 three-dimensional environmental scanning electron microscope.

Average size distribution calculations: Average diameters of the particles in water, acid, or base solutions are determined based on confocal microscopy images by measuring diameters of more than 100 particles and calculating a mean value.

Molecule uptake: 2-aminoacridone (≧98%, HPLC) (AAC, 3-acetyl-umbelliferon (≧98%, HPLC) (AU), 6-carboxyfluorescein (≧95%, HPLC) (CFI), eosin yellowish solution (EYS), rhodamine B (RB), rhodamine B base (RBB) are purchased from Sigma-Aldrich. Solutions of AAC (0.0006% w/v), AU (0.00004% w/v), CFI (0.0004% w/v), EYS (0.0001% w/v), RB (0.00004% w/v) and RBB (0.00013% w/v) are prepared in deionized water, and solutions of dye pairs are prepared with a 1:1 (v:v ratio). To examine the selective absorption behavior of the core-shell particles, the particles are incubated in solutions of dye pairs for 3 hours, and then separated from the solutions by centrifugation at 12,000 RPM for 10 min.

TABLE 1 below shows the composition of polymer solutions used for preparation of (core-shell)$_{ab}$ particles, anisotropic (biphasic)$_{a'b}$ particles (e.g., Janus-type) and particles with undefined geometry ([cb] particles or [db] particles).

TABLE 1

| Polymer solutions | Concentration [(W/V)%] | Electrical Conductivity [mS cm$^{-1}$] |
|---|---|---|
| [a] | | 32 |
| PAA | 13.1 | |
| PAAm-co-AA | 0.044 | |
| NaOH | 2.19 | |
| FITC-dextran | 0.4 | |
| D.I. Water | Balance | |
| [b] | | 5 |
| PAAm-co-AA | 5 | |
| PAA | 0.9 | |
| TRITC-dextran | 0.4 | |
| D.I. Water | Balance | |
| [c] | | 12 |
| PAA | 13.1 | |
| PAAm-co-AA | 0.044 | |
| NaOH | 0.75 | |
| FITC-dextran | 0.4 | |
| D.I. Water | Balance | |
| [d] | | 27 |
| PAA | 13.1 | |
| PAAm-co-AA | 0.044 | |
| NaOH | 1.75 | |
| FITC-dextran | 0.4 | |
| D.I. Water | Balance | |
| [a'] | | 5 |
| PAAm-co-AA | 5 | |
| PAA | 0.9 | |
| FITC-dextran | 0.4 | |
| D.I. Water | Balance | |

[a]/[b] jetting solutions used for preparation of the particles with core-shell geometry.
[c]/[b] or [d]/[b] jetting solutions with same concentration of polymers as [a]/[b] and with different concentration of NaOH, resulting in changes in conductivity of the jetting solutions.
[a']/[b] jetting solutions used for preparation of the particles with anisotropic (e.g., Janus) geometry.

Prior to suspension in aqueous buffer systems, thermal crosslinking between amide and carboxylic groups is used to prevent dissolution of the particles in aqueous solutions and to provide differential swelling properties. Polymer crosslinking is performed by placing the particles in an oven at 170° C. for 2 hours. Under these conditions, the shell phase is more extensively crosslinked, due to the higher content of acrylamide in the shell region as compared to the core region.

As shown in FIG. 4, particles show reproducible changes in swelling after incubation in aqueous solutions that are either acidic (pH 1.3) or basic (pH 12). Under these conditions, the gross morphology of the particles remained unaltered. Average particle diameters are measured using confocal microscopy and mean values for different conditions, which are presented in FIG. 4.

During electrohydrodynamic co-jetting, a typical batch of particles has an average diameter of 1.9±0.4 μm. After subsequent incubation in de-ionized water, the average size of the same batch of particles increases to 6+/−1.0 μm, a more than 300% increase in particle diameter. Next, particles are incubated in alternating acidic (pH 1.3) or basic (pH 12) solutions. The pH changes in the solution is performed by using HCl and NaOH solutions. Under these conditions, the particle diameter reproducibly switches between 3.5±0.5 μm and 6±1.0 μm. Histograms indicate statistic calculations for size distribution of (core-shell)$_{ab}$ particles in acidic (A$_{index}$) or basic (B$_{index}$) environments in a given diameter range; (core-shell)$_{ab}$ particles at pH 1.3: 0.6-2.5 μm (A$_1$), 2.5-4.4 μm (A$_2$), 4.4-6.3 μm (A$_3$), 6.3-8.2 μm (A$_4$); (core-shell)$_{ab}$ particles at pH 12: 0.6-4.6 μm (B$_1$), 4.6-8.6 μm (B$_2$), 8.6-12.6 μm (B$_3$), 12.6-16.6 μm (B$_4$). After 5 consecutive switching cycles, the particles maintain their integrity and preserve the core-shell character, demonstrating excellent structural stability.

The increase in size of the particles in water or basic solutions is believed to be due to pH-induced swelling of polyacrylates. Prior to exposure of freshly jetted and cross-linked particles to water, PAA segments are believed to form coiled chains. Subsequent exposure to water causes hydration of the particles and is believed to result in repulsive interactions between negatively-charged carboxylic acid groups. While not limiting the present teachings to any particular theory, it is believe that under these conditions, the polyelectrolyte chains exhibit a more stretched form, and inter- and intra-molecular repulsion causes increased absorption of water and expansion of the particles. When exposed to an acidic media, the carboxylic acid groups are protonated, eliminating charge-charge repulsion and causing shrinkage of the particles. As noted above, in FIG. 4, histograms are shown for each condition indicating the number of particles that fall within one of four size ranges, i.e. smallest (<25%), small/medium (26-50%), medium/large (51-75%), and largest particle fraction (>75%). When exposed to a sufficiently high pH, the acid groups are deprotonated and repulsion between negatively charged polymer chains causes expansion of the particles.

FIGS. 5A-5C show SEM and confocal microscopy images of (core-shell)$_{ab}$ particles. FIG. 5A shows representative particles, which are placed in strongly acidic solution (pH 0.4) and dried in air, indicating that the surface of the particles remains unaltered after introducing them to the acidic medium. However, the confocal microscopy image (FIG. 5B) from the particles in acidic media (pH 0.4), suggests that particles became hollow when placed in strong acid. An explanation for the transition into hollow capsules is that PAA, which is the dominant polymer in the core, becomes fully protonated leading to a retraction of the polymer chains into the core/shell interface. Dissolution of the core polymer or dye can be excluded as a possible explanation, as particles fully recovered into their original core-shell structure after incubation in basic (pH 12) solution (FIG. 5C). However, mixing of dyes may occur to some extent, as indicated by the color change of the cores from the original green to a more yellowish appearance. Thus, as shown in FIGS. 5A-5C, a crosslinking reaction imparts the following swelling behaviors: (a) in water, the particles are simply swelled and indicate an increase in their size about 3-4 times; (b) in acidic media the particles shrink and show a decrease in size and, by decreasing pH of the media (strong acidic media) the particles become hollow in the center; and (c) in basic media the particles behave more or less like their swelling behavior in water.

Thus, in various aspects, where such multiphasic microcomponents have a core region and a shell region, in the presence of an acidic media, the particles may shrink and show a decrease in size. In certain aspects, the core region can become hollow due to significant contraction of this core phase when the pH of the media is reduced (strong acidic media). Desirably, such contraction is reversible when the micro-component particles are exposed to a neutral or basic media.

The ability to switch between capsules and core/shell particles may be particularly useful for drug delivery applications or selective absorption of small molecules, as well as environmentally friendly applications, such as remediation of toxins or contaminants. In various aspects, the micro-component particles formed in accordance with the present disclosure can be used for delivery in micro-systems.

FIGS. 6A-6C show digital photos of a polymer scaffold consisting of (core-shell)$_{ab}$ particles after jetting, in de-ionized water, and in acidic media. Immediately upon placing (core-shell)$_{ab}$ particles in water (FIG. 6B), the particles expand their size resulting in swelling of the scaffold. After altering the environment to an acidic media, the swelling of the particles is reversed with significant shrinkage (FIG. 6C).

Next, the ability of core-shell particles for selective absorption of different dyes is evaluated. Initially (core-shell)$_{ab}$ particles with colorless cores are prepared. In order to be able to visualize the core-shell character of the particles, tetramethylrhodamine isothiocyanate—(TRITC) or fluorescein isothiocyanate (FITC)-dextran are added to the respective polymer solutions. The polymer solutions used for jetting process are PAAm-co-AA (5% w/v)/PAA (0.9% w/v)/TRITC-dextran (0.4% w/v) and PAA (13.1% w/v)/PAAm-co-AA (0.044% w/v)/NaOH (2.19% w/v)/FITC-dextran (0.4% w/v). FITC and TRITC containing phases form the particle core indicated by green fluorescence or shell indicated by red fluorescence, respectively.

Hence, for better imaging, the shell material is either loaded with TRITC- or FITC-dextran. First, the FITC-loaded particles are suspended in water (FIG. 7A) and a dilute solution of rhodamine B base is added to the particle suspension. After incubation for 3 hours, the red dye is readily taken up into the core of the particles (FIG. 7B). Enhanced red fluorescence is observed in the shell, as well as in the core, while the initial dye solution appeared to be depleted. In stark contrast, (core-shell)$_{ab}$ particles without FITC-dextran did not show any appreciable uptake of 6-carboxyfluorescein (shown in FIG. 7D) for particles with TRITC-labeled shells.

Thus, in FIG. 7A, the (core-shell)$_{ab}$ particles are shown in deionized water and have a shell formed from a jetting liquid solution of PAAm-co-AA at 5% w/v/PAA(0.9 w/v)/FITC-dextran (0.4% w/v) and a core formed from a jetting liquid solution of PAA (13.1% w/v)/PAAm-co-AA (0.044% w/v)/NaOH(2.19% w/v). FIG. 7B has (core-shell)$_{ab}$ particles formed from the same composition as in FIG. 7A, but in dilute solution of rhodamine B base. FIG. 7C has (core-shell)$_{ab}$ particles in deionized water formed from a shell of PAAm-co-AA (5% w/v)/PAA(0.9 w/v)/TRITC (0.4% w/v) and a core formed from a core formed from a jetting liquid solution of PAA (13.1% w/v)/PAAm-co-AA (0.044% w/v)/NaOH (2.19% w/v). FIG. 7D has (core-shell)$_{ab}$ particles formed from the same composition as in FIG. 7C, but in dilute solution of 6-carboxyfluoroescein.

The marked selectivity of (core-shell)$_{ab}$ particles for different dyes (FIG. 8) to electrostatic repulsion is attributed to differences in the net charge of the two dyes. The core-shell particles are net negatively-charged and repel the negatively-charged 6-carboxyfluorescein. To further elucidate the molecular basis of this selectivity between dyes of similar size, a further quantitative uptake example is conducted with 6 dyes (FIG. 8):

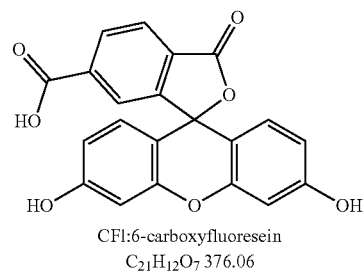

CFl: 6-carboxyfluoresein
$C_{21}H_{12}O_7$ 376.06

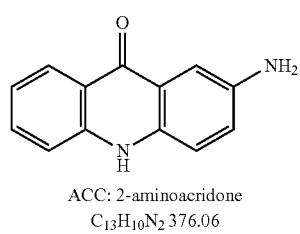

ACC: 2-aminoacridone
$C_{13}H_{10}N_2$ 376.06

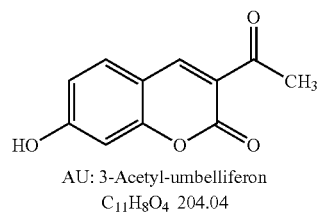

AU: 3-Acetyl-umbelliferon
$C_{11}H_8O_4$ 204.04

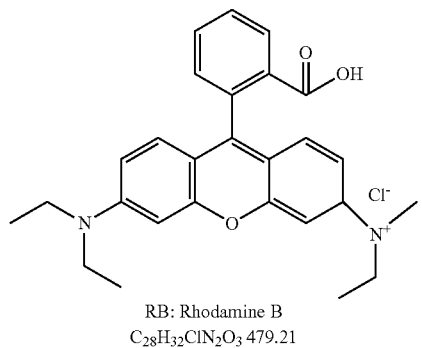

RB: Rhodamine B
$C_{28}H_{32}ClN_2O_3$ 479.21

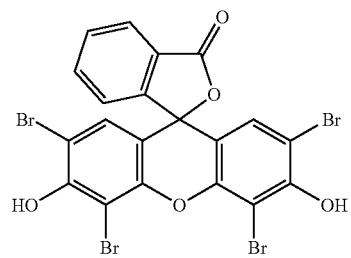

EYS: Eosin yellowish solution
$C_{20}H_8Br_4O_5$ 643.71

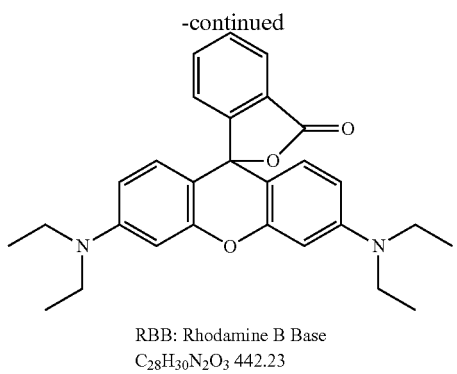

RBB: Rhodamine B Base
C$_{28}$H$_{30}$N$_2$O$_3$ 442.23

The dyes selected for these experiments have molecular weights ranging from 204 to 643 g/mol, and include widely used fluorescence dyes, such as rhodamine B, 6-carboxyfluorescein, eosin, or aminoacridone. First, pairs of low-molecular weight dyes are dissolved in aqueous solutions and then a defined amount of (core-shell)$_{ab}$ particles is added to the solution and incubated for 3 hours. Here, neither core nor shell is loaded with any dye during electrohydrodynamic co-jetting. The particles are separated by centrifugation and the supernatant is analyzed by UV/VIS spectroscopy. Selectivity is defined as the ratio of the two dye concentrations after particle exposure, each being normalized to the initial dye concentration:

$$S = \frac{C_1/C_1'}{C_2/C_2'}$$

S = dye selectivity $C_1$ and $C_2$ = dye concentration after incubation with particles $C_1'$ and $C_2'$ = initial dye concentrations In FIG. 8, each data point represents the n-fold increase in dye uptake after adding core-shell particles to the solution. The rhodamine B base/6-carboxyfluorescein pair, i.e., the pair shown in FIG. 7, exhibited the highest selectivity with S=4.5. The inset of FIG. 8 shows the dye solution before and after incubation with particles. A clear change in color due to selective removal of rhodamine B base (RBB) can be observed. In contrast, the initially colorless particles are indicated with bright red color due to selective uptake of only the red dye. A comparable selectivity is achieved for solutions containing rhodamine B base and either eosin yellowish solution (EYS) or 3-acetyl-umbelliferon (AU). When combined with 6-carboxyfluorescein (CFI), the uptake selectivity of rhodamine B (RB) is 2.3, which is significantly lower than the uptake selectivity of rhodamine B base relative to CFI.

Moreover, the uptake of ACC is 2.5-fold higher than the uptake for AU, in spite of the fact that AU is the smaller molecule. However, the selectivity of ACC versus AU is significantly lower than the relative selectivity of RB versus AU. Again, this effect does not correlate with molecular weight because the molecular weight of RB is higher than the molecular weight of ACC or AU, respectively.

In the inset pictures of FIG. 8, the first solution at (a) is rhodamine B (RBB) and 6-carboxyfluorescein (CFI) before adding (core-shell)$_{ab}$ particles. The second solution at (b) is the same as in the previous solution, where the (core-shell)$_{ab}$ are added and then removed. In (c), a CFM image is shown of the (core-shell)$_{ab}$ particles after being exposed to a solution of rhodamine B base and 6-carboxyfluorescein. The particle core was initially colorless. Scale bars for (a) and (b) are 5 mm and 8 µm for (c).

Based on these outcomes, several common trends can be identified and while not limiting the present teachings to any particular mechanism are theorized as follows: (i) the presence of carboxylic acid groups in a molecule reduces uptake into particles, presumably due to charge repulsion; (ii) amino groups enhance dye uptake—with tertiary amines showing higher uptake than primary amines; (iii) presence of a free acid group in RB decreases uptake and reduces selectivity as compared to RBB; and (iv) within the limited number of molecules tested, the process appears to be independent of the molecular weight of the molecules.

Thus, multiphasic micro-components in accordance with the present teachings are capable of selective absorption of various active materials into one phase preferentially over other phases in the particle. This is a particularly useful feature for imbibing and/or releasing active materials from select phases. This is demonstrated by core-shell particles in the examples above, which show 450% increase in uptake of 6-carboxyfluorescein over rhodamine B base; in fact, this appears to be a general trend, as similar selectivities are observed for a number of different dyes.

Furthermore, in certain aspects, after cross-linking, multiphasic micro-components, such as core-shell particles, are stable in aqueous solutions and exhibit reproducible swelling behavior, while maintaining the original core-shell geometry. In addition, pH-responsiveness of the particles is demonstrated by repeatedly switching the environmental pH from highly acidic to highly basic conditions. Differential uptake of small molecules and environmental responsiveness are key features in the design of novel drug delivery vehicles or particles that can be used for clean-up and remediation of environmental contaminants or toxic waste.

In various aspects, the present disclosure provides methods of forming multiphasic micro-components via an electrified jetting process. In certain aspects, the present disclosure provides a method of controlling the morphology of a multiphasic micro-component comprising providing a first liquid stream having a first electrical conductivity comprising a first polyelectrolyte and a second liquid stream having a second electrical conductivity comprising a second polyelectrolyte. The first and second electrical conductivities are respectively selected to create a predetermined phase orientation in a solid micro-component. Then, at least a portion of the first liquid stream and at least a portion of the second stream are exposed to an electric force field sufficient to form the solid micro-component comprising a first phase and a second distinct phase. In certain aspects, a composite stream can be formed by contacting a portion of the first liquid stream with a portion of the second liquid stream. At least a portion of a composite stream is exposed to an electric force field sufficient to form a solid micro-component comprising a first phase and a second distinct phase.

The first phase comprises material from the first liquid stream and the second phase comprises material from the second liquid stream, such that the first phase and the second phase are compositionally distinct from one another. The first electrical conductivity and the second electrical conductivity in the first and second liquid streams are selected to create a predetermined phase orientation in the solid micro-component.

In certain variations, after exposing the composite stream to an electric force field, an active ingredient can be introduced into at least one of the first or second phases by contacting the active ingredient with a portion of the first or second phases for absorption therein. In certain aspects, the active ingredient may be absorbed by one or more phases.

In various aspects, the present disclosure provides a method of forming a core-shell multiphasic micro-component by forming a composite stream by contacting a portion of a first liquid stream having a first electrical conductivity and comprising a first polyelectrolyte with a portion of a second liquid stream having a second electrical conductivity and comprising a second polyelectrolyte. A portion of the composite stream is exposed to an electric force field sufficient to form a solid micro-component comprising a first phase and a second distinct phase. A difference between the first electrical conductivity and the second electrical conductivity is selected to be greater than or equal to about 600% to form a core-shell morphology where the first or second liquid jetting streams comprises water. In embodiments where the jetting liquid does not include water, a difference between the first electrical conductivity and the second electrical conductivity is selected to be greater than or equal to about 200% to form a core-shell morphology. The first phase comprises material from the first liquid stream and the second phase comprises material from the second liquid stream, such that the first phase and the second phase are compositionally distinct from one another. One of the first phase or the second phase defines a core region of the micro-component and the other of the first phase and the second phase defines a shell region externally surrounding at least a portion of the core region.

In other aspects, the present disclosure provides multiphasic micro-components formed in accordance with such methods. For example, a multiphasic micro-component comprises a first hydrophilic phase formed from a liquid stream comprising a first polyelectrolyte and a second hydrophilic phase formed from at least a portion of the core region formed from a distinct liquid stream comprising a second polyelectrolyte. The first hydrophilic phase and the second hydrophilic phase are compositionally distinct from one another and at least one of the first and second phases comprises an active ingredient. Further, the multiphasic micro-component optionally has a substantially round shape. In certain aspects, the first polyelectrolyte and the second polyelectrolyte are independently selected from the group consisting of: polyacrylic acid (PAA), poly(acrylamide acrylic acid (PAAm), and/or poly (acryl amide-co-acrylic acid) (PAAm-AA), sodium polystyrene sulfonate (PSS), polyethylene imine (PEI), polypeptides, copolymers, and combinations thereof. In certain variations. at least one of the first phase or the second phase comprises a component reactive to a pH of an external environment.

In yet other aspects, the present disclosure provides multiphasic core-shell micro-components comprising a first phase defining a core region formed from a liquid stream comprising a first polyelectrolyte and a second phase defining a shell region externally surrounding at least a portion of the core region formed from a distinct liquid stream comprising a second polyelectrolyte. The first and second phases are compositionally distinct from one another. At least one of the first and second phases comprises an active ingredient. Further, in certain aspects, at least one of the first phase and the second phase undergoes reversible swelling in response to an external stimulus from a surrounding environment.

In other aspects, a multiphasic core-shell micro-component is provided by the present teachings. The micro-component includes a first phase defining a core region formed from a liquid stream comprising a first polyelectrolyte and a second phase defining a a shell region externally surrounding at least a portion of the core region formed from a distinct liquid stream comprising a second polyelectrolyte. The first phase and the second phase are compositionally distinct from one another and have a difference in respective electrical conductivities. At least one of the first phase and the second phase comprises an active ingredient. Further, at least one of the first phase and the second phase undergoes reversible swelling in response to an external stimulus from a surrounding environment. In certain aspects, the external stimulus is selected from the group consisting of pH, humidity, pressure, light, temperature, applied energy fields, electrical fields, magnetic fields, and combinations thereof.

In yet other aspects, a core-shell multiphasic micro-component includes a first hydrophilic phase defining a core region comprising a first polyelectrolyte selected from polyacrylic acid (PAA), poly(acrylamide acrylic acid (PAAm), and/or poly(acryl amide-co-acrylic acid) (PAAm-AA), sodium polystyrene sulfonate (PSS), polyethlene imine (PEI), polypeptides, copolymers, and combinations thereof. In certain aspects, the first polyelectrolyte is selected from polyacrylic acid (PAA), poly(acrylamide acrylic acid (PAAm), and/or poly(acryl amide-co-acrylic acid) (PAAm-AA), sodium polystyrene sulfonate (PSS), copolymers, and combinations thereof. Further, the first hydrophilic phase is cross-linked.

The micro-component also includes a second hydrophilic phase defining a shell region externally surrounding at least a portion of the core region comprising a second polyelectrolyte are independently selected from polyacrylic acid (PAA), poly(acrylamide acrylic acid (PAAm), and/or poly(acryl amide-co-acrylic acid) (PAAm-AA), sodium polystyrene sulfonate (PSS), polyethlene imine (PEI), polypeptides, copolymers, and combinations thereof. In certain aspects, the second polyelectrolyte is selected from polyacrylic acid (PAA), poly(acrylamide acrylic acid (PAAm), and/or poly (acryl amide-co-acrylic acid) (PAAm-AA), sodium polystyrene sulfonate (PSS), copolymers, and combinations thereof. The second hydrophilic phase is cross-linked. The first and second phases are compositionally distinct from one another. In accordance with the present disclosure, in certain aspects, at least one of the first and second phases undergoes reversible swelling in response to an external stimuli from a surrounding environment.

In summary, the present teachings provide a method for preparation of multiphasic micro-components having a predetermined phase orientation and morphology. In certain aspects, multiphasic micro-components are substantially round-shaped and the predetermined phase orientation is core-shell, so that formed particles have well-defined structures using electohydrodynamic co-jetting. In certain aspects, such co-jetting is conducted with two aqueous polymer solutions containing polyelectrolytes, such as poly(acrylic acid) and poly(acrylamide-co-acrylic acid). Controlled variation of relative conductivities of the two jetting solutions results in control over the phase orientation and particle morphologies, where polymer micro-component particles can have anisotropic multiphasic (e.g., Janus-type biphasic) or core-shell geometries for the same polymer system.

What is claimed is:

1. A method of controlling the morphology of a multiphasic micro-component comprising:
providing a first liquid stream having a first electrical conductivity comprising a first polyelectrolyte and a second liquid stream having a second electrical conductivity comprising a second polyelectrolyte, wherein said first polyelectrolyte and said second polyelectrolyte are independently selected from the group consisting of: polyacrylic acid (PAA), poly(acrylamide acrylic acid (PAAm), and/or poly(acryl amide-co-acrylic acid)

(PAAm-AA), sodium polystyrene sulfonate (PSS), polyethylene imine (PEI), polypeptides, copolymers, and combinations thereof, wherein said first electrical conductivity and said second electrical conductivity are selected to create a predetermined phase orientation in a solid micro-component; and exposing at least a portion of said first liquid stream and at least a portion of said second stream to an electric force field sufficient to form the solid micro-component comprising a first phase and a second distinct phase, wherein said first phase comprises material from said first liquid stream so that said first phase is hydrophilic and said second phase comprises material from said second liquid stream so that said second phase is hydrophilic, such that said first phase and said second phase are compositionally distinct from one another;

applying energy to cure said first polyelectrolyte and said second polyelectrolyte, so that the predetermined phase orientation in the solid micro-component is formed and the solid micro-component comprises a cross-linked first hydrophilic phase and a second cross-linked hydrophilic phase.

2. The method of claim 1, wherein a ratio of said first electrical conductivity to said second electrical conductivity is about 1:1 to about 3:1 and said predetermined phase orientation is anisotropic so that said first phase has a first exposed surface and said second phase has a second exposed surface.

3. The method of claim 1, wherein said exposing further comprises contacting a portion of an additional liquid stream with said first and second liquid streams, wherein said additional liquid stream is compositionally distinct from said first and second liquid streams and said exposing forms the solid micro-component comprising said first phase, said second phase, and an additional phase comprising a material from said additional liquid stream, wherein said first phase, said second phase, and said third phase are each compositionally distinct from one another.

4. The method of claim 1, wherein at least one of said first phase or said second phase comprises a component reactive to a pH of an external environment.

5. The method of claim 1, wherein a ratio of said first electrical conductivity to said second electrical conductivity is at least about 6:1 and said predetermined phase orientation is a core-shell morphology.

6. The method of claim 1, wherein after said exposing, introducing said active ingredient into at least one of said first or second phases by contacting said active ingredient with a portion of said first or second phases for absorption therein.

7. A multiphasic micro-component comprising:
a first hydrophilic phase formed from a liquid stream comprising a first polyelectrolyte;
a second hydrophilic phase formed from a distinct liquid stream comprising a second polyelectrolyte; wherein said first hydrophilic phase and said second hydrophilic phase are compositionally distinct from one another and are respectively cross-linked, wherein at least one of said first phase and said second phase comprises an active ingredient and said first phase has a first exposed surface and said second phase has a second exposed surface, so that said the multi-phasic micro-component has an anisotropic morphology.

8. The multiphasic micro-component of claim 7, wherein at least one of said first phase and said second phase undergoes reversible swelling in response to an external stimulus from a surrounding environment.

9. The multiphasic micro-component of claim 8, wherein said external stimulus is a pH of said surrounding environment.

10. The multiphasic micro-component of claim 7, wherein said active ingredient is selected from the group consisting of: a therapeutic active ingredient, a systemic active ingredient, a chemotherapy active ingredient, a localized active ingredient, an oral care active ingredient, a nutritional active ingredient, a personal care active ingredient, a cosmetic active ingredient, a diagnostic imaging indicator agent, pesticides, growth-promoting agents, a home care active ingredient, an industrial or institutional active ingredient, and combinations thereof.

11. The multiphasic micro-component of claim 7, wherein said active ingredient is selected from the group consisting of: low-molecular weight molecules, natural and artificial macromolecules, growth factors, growth factor receptors, transcriptional activators, translational promoters, anti-proliferative agents, growth hormones, anti-rejection drugs, anti-thrombotic agents, anti-coagulants, stem cell or gene therapy agents, antioxidants, free radical scavengers, nutrients, co-enzymes, ligands, peptides, proteins, nucleic acids, DNA, RNA, sugars, saccharides, nutrients, hormones, antibodies, immunomodulating agents, growth factor inhibitors, growth factor receptor antagonists, transcriptional repressors, translational repressors, replication inhibitors, inhibitory antibodies, cytotoxin, hormonal agonists, hormonal antagonists, inhibitors of hormone biosynthesis and processing, antigestagens, antiandrogens, anti-inflammatory agents, analgesics, non-steroidal anti-inflammatory agents (NSAIDs), COX-I and II inhibitors, antimicrobial agents, antiviral agents, antifungal agents, antibiotics, antineoplastic/antiproliferative/anti-miotic agents, anesthetic, analgesic or pain-killing agents, antipyretic agents, prostaglandin inhibitors, platelet inhibitors, DNA de-methylating agents, cholesterol-lowering agents, vasodilating agents, endogenous vasoactive interference agents, angiogenic substances, cardiac failure active ingredients, polysaccharides, sugars, targeting toxin agents, aptamers, quantum dots, nano-materials, nano-crystals, localized drugs, tooth whitening agents, skin whitening agents, anti-caries agents, anti-tartar agents, anti-plaque agents, anti-adhesion agents, desensitizing agents, malodor control agents, flavoring agents, anti-aging agents, salivary stimulants, periodontal actives, depigmentation agents, skin lightening agents, reflectants, humectants, allergy inhibitors, anti-acne agents, anti-aging agents, anti-wrinkling agents, antiseptics, keratolytic agents, fresheners, healing agents, inflammation inhibitors, wound healing promoters, deodorants, antiperspirants, skin emollients, tanning agents, antifungals, depilating agents, counterirritants, non-steroidal soothing agents, anti-itch agents, poison ivy agents, poison oak agents, burn alleviation agents, vitamins, cooling agents, heating agents, chelating agents, anti-psoriasis agents, anti-dandruff agents, skin conditioners, moisturizing agents, emollients, humectants, occlusive agents, skin lipid fluidizers, deodorant active agents, antiperspirant active agents, skin and/or scalp sensates, skin and/or scalp soothing and/or healing agents, astringents, opacifying agents, biocides, natural and synthetic extracts and essential oils, nutrients, enzymes, proteins, amino acids, vitamins, analgesics, sunscreen agents, UV absorbers, antioxidants, antibiotics, exfoliants, cell turnover enhancers, coloring agents, sunscreens, nourishing agents, moisture absorbers, sebum absorbers, skin penetration enhancers, colorants, pigments, dyes, flavors, fragrances, detergents, fabric softeners, hard surface cleaning agents, bleaching agents, surface active agents, phosphates, builders, anti-deposition agents, imaging or contrast agents, pesticides, growth-promoting agents, and combinations thereof.

12. A multiphasic core-shell micro-component comprising:
- a first cross-linked phase defining a core region formed from a liquid stream comprising a first polyelectrolyte that comprises polyacrylic acid (PAA);
- a second cross-linked phase defining a shell region externally surrounding at least a portion of said core region formed from a distinct liquid stream comprising a second polyelectrolyte that comprises poly(acryl amide-co-acrylic acid) (PAAm-AA); wherein said first phase and said second phase are compositionally distinct from one another, wherein at least one of said first phase and said second phase comprises an active ingredient.

13. The multiphasic core-shell micro-component of claim 12, wherein at least one of said first phase and said second phase undergoes reversible swelling in response to an external stimulus from a surrounding environment.

14. The multiphasic core-shell micro-component of claim 12, wherein at least one of said first phase and said second phase reacts to an external stimulus selected from the group consisting of pH, humidity, pressure, light, temperature, applied energy fields, electrical fields, magnetic fields, or combinations thereof.

15. The multiphasic core-shell micro-component of claim 12, wherein said first cross-linked phase or said second cross-linked phase further comprises an additional polymer distinct from said first polyelectrolyte or said second polyelectrolyte, the additional polymer selected from the group consisting of: polyacrylic acid (PAA), poly(acrylamide acrylic acid (PAAm), and/or poly(acryl amide-co-acrylic acid) (PAAm-AA), sodium polystyrene sulfonate (PSS), polyethylene imine (PEI), polypeptides, copolymers and combinations thereof.

16. The multiphasic core-shell micro-component of claim 12, wherein the micro-component is a capsule for delivery of an active agent selected from the group consisting of: a therapeutic active ingredient, a systemic active ingredient, a chemotherapy active ingredient, a localized active ingredient, an oral care active ingredient, a nutritional active ingredient, a personal care active ingredient, a cosmetic active ingredient, a diagnostic imaging indicator agent, pesticides, growth-promoting agents, a home care active ingredient, an industrial or institutional active ingredient, and combinations thereof.

17. The multiphasic core-shell micro-component of claim 12, wherein a conductivity mismatch ($\Delta\sigma$) between a first conductivity of the liquid stream comprising the first polyelectrolyte and a second conductivity of the distinct liquid stream comprising the second polyelectrolyte is greater than or equal to about 200%.

18. The multiphasic core-shell micro-component of claim 12, wherein said first cross-linked phase further comprises poly(acryl amide-co-acrylic acid) (PAAm-AA) in addition to said first polyelectrolyte comprising said polyacrylic acid (PAA) and said second cross-linked phase further comprises polyacrylic acid (PAA) in addition to said second polyelectrolyte comprising said poly(acryl amide-co-acrylic acid) (PAAm-AA).

19. A multiphasic micro-component comprising:
- a first hydrophilic phase formed from a liquid stream comprising a first polyelectrolyte;
- a second hydrophilic phase formed from a distinct liquid stream comprising a second polyelectrolyte; wherein said first polyelectrolyte and said second polyelectrolyte are independently selected from the group consisting of: polyacrylic acid (PAA), poly(acrylamide acrylic acid (PAAm), and/or poly(acryl amide-co-acrylic acid) (PAAm-AA), sodium polystyrene sulfonate (PSS), polyethylene imine (PEI), polypeptides, copolymers and combinations thereof and wherein said first hydrophilic phase and said second hydrophilic phase are compositionally distinct from one another and are respectively cross-linked, wherein at least one of said first phase and said second phase comprises an active ingredient.

20. The multiphasic micro-component of claim 19, wherein said first polyelectrolyte polymer comprises polyacrylic acid (PAA) and said second polyelectrolyte polymer comprises poly(acryl amide-co-acrylic acid) (PAAm-AA).

21. The multiphasic micro-component of claim 20, wherein said first phase further comprises poly(acryl amide-co-acrylic acid) (PAAm-AA) in addition to said first polyelectrolyte polymer comprising said polyacrylic acid (PAA) and said second phase further comprises polyacrylic acid (PAA) in addition to said second polyelectrolyte polymer comprising said poly(acryl amide-co-acrylic acid) (PAAm-AA).

* * * * *